(12) United States Patent
Yoo

(10) Patent No.: US 11,895,560 B2
(45) Date of Patent: Feb. 6, 2024

(54) DISTRIBUTED TYPE TRAFFIC LINE TRACING APPARATUS, AND METHOD USING THE SAME

(71) Applicant: Research & Business Foundation Sungkyunkwan University, Suwon-si (KR)

(72) Inventor: Jae-Chern Yoo, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 411 days.

(21) Appl. No.: 17/231,458

(22) Filed: Apr. 15, 2021

(65) Prior Publication Data
US 2022/0014876 A1 Jan. 13, 2022

(30) Foreign Application Priority Data
Jul. 13, 2020 (KR) .......................... 10-2020-0086171

(51) Int. Cl.
*H04W 4/029* (2018.01)
*G16H 50/30* (2018.01)
*G16H 50/70* (2018.01)
*G16H 50/20* (2018.01)
*G06V 40/60* (2022.01)
(Continued)

(52) U.S. Cl.
CPC ............. *H04W 4/029* (2018.02); *G06T 11/00* (2013.01); *G06V 40/1365* (2022.01); *G06V 40/67* (2022.01); *G08B 21/0415* (2013.01); *G08B 21/0492* (2013.01); *G10L 15/22* (2013.01); *G16H 50/20* (2018.01); *G16H 50/30* (2018.01);
(Continued)

(58) Field of Classification Search
None
See application file for complete search history.

(56) References Cited

U.S. PATENT DOCUMENTS

2009/0249011 A1* 10/2009 Ohishi ................ G06F 11/1464
  711/E12.001
2020/0210951 A1* 7/2020 Perez .................. H04L 63/0861
2021/0358068 A1* 11/2021 Boszczyk ............ G06Q 50/265

FOREIGN PATENT DOCUMENTS

KR    10-2012-0132921 A    12/2012
KR    10-2017-0021692 A    2/2017
(Continued)

OTHER PUBLICATIONS

Korean Office Action dated Nov. 14, 2020 in counterpart Korean Patent Application No. 10-2020-0086171 (7 pages in Korean).

*Primary Examiner* — Frantz Bataille
(74) *Attorney, Agent, or Firm* — NSIP Law

(57) ABSTRACT

A distributed type traffic line tracing apparatus of the present disclosure is personally installed in a residence of a tracing target person, to automatically verify whether a traffic line of the tracing target person coincides with a traffic line of a confirmed person and automatically report a result to a disease management authority only when the traffic lines coincide with each other in an emergency situation such as an infectious disease pandemic, so that a quarantining target person is discovered and found early while protecting a privacy of an individual much more when compared to a centralized type, thereby rapidly establishing an infectious disease management system for patients with suspected diseases and efficiently managing the patients from the spread of infectious diseases.

16 Claims, 10 Drawing Sheets

(51) Int. Cl.
*G06V 40/12* (2022.01)
*G06T 11/00* (2006.01)
*G08B 21/04* (2006.01)
*G10L 15/22* (2006.01)
*H04N 5/33* (2023.01)

(52) U.S. Cl.
CPC ............... G16H 50/70 (2018.01); H04N 5/33 (2013.01); *G10L 2015/223* (2013.01)

(56) References Cited

FOREIGN PATENT DOCUMENTS

| KR | 10-2017-0081023 A | 7/2017 |
| KR | 10-2019-0068522 A | 6/2019 |
| KR | 10-2020-0047457 A | 5/2020 |

\* cited by examiner

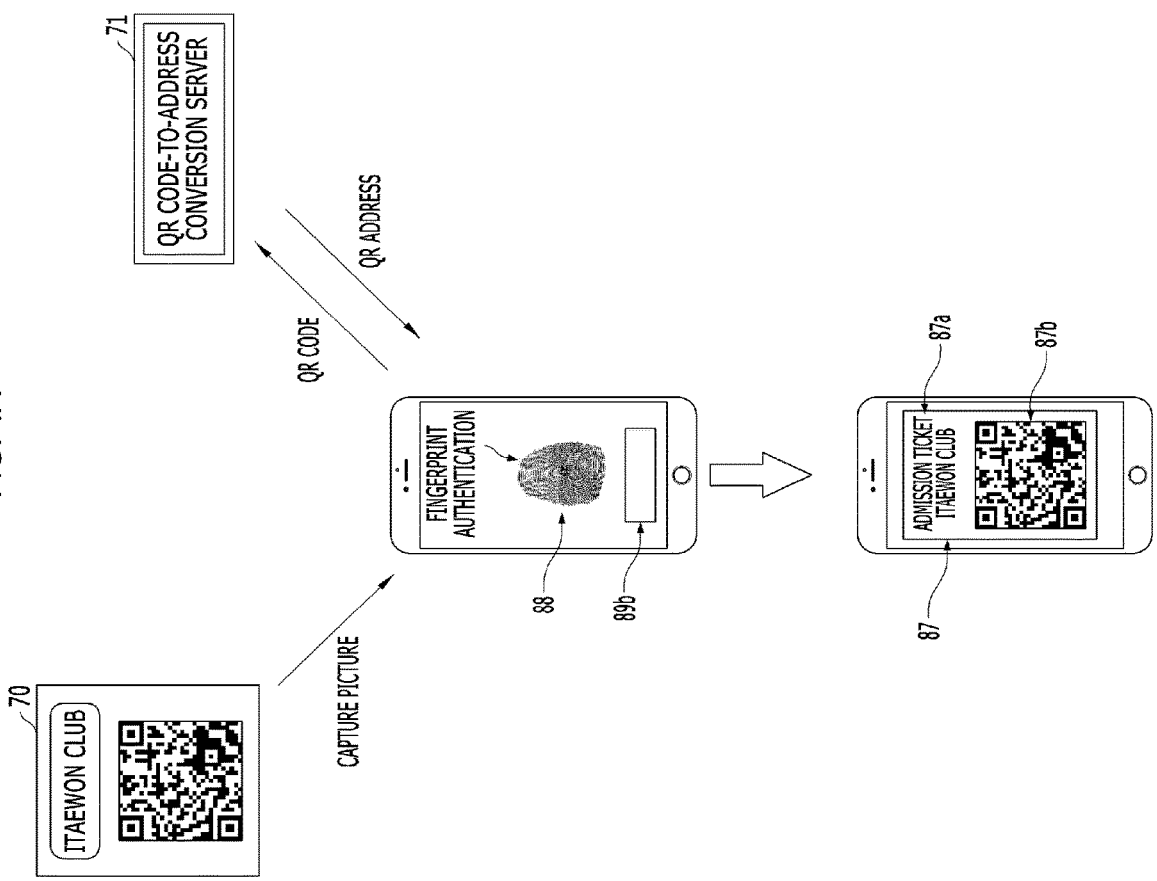

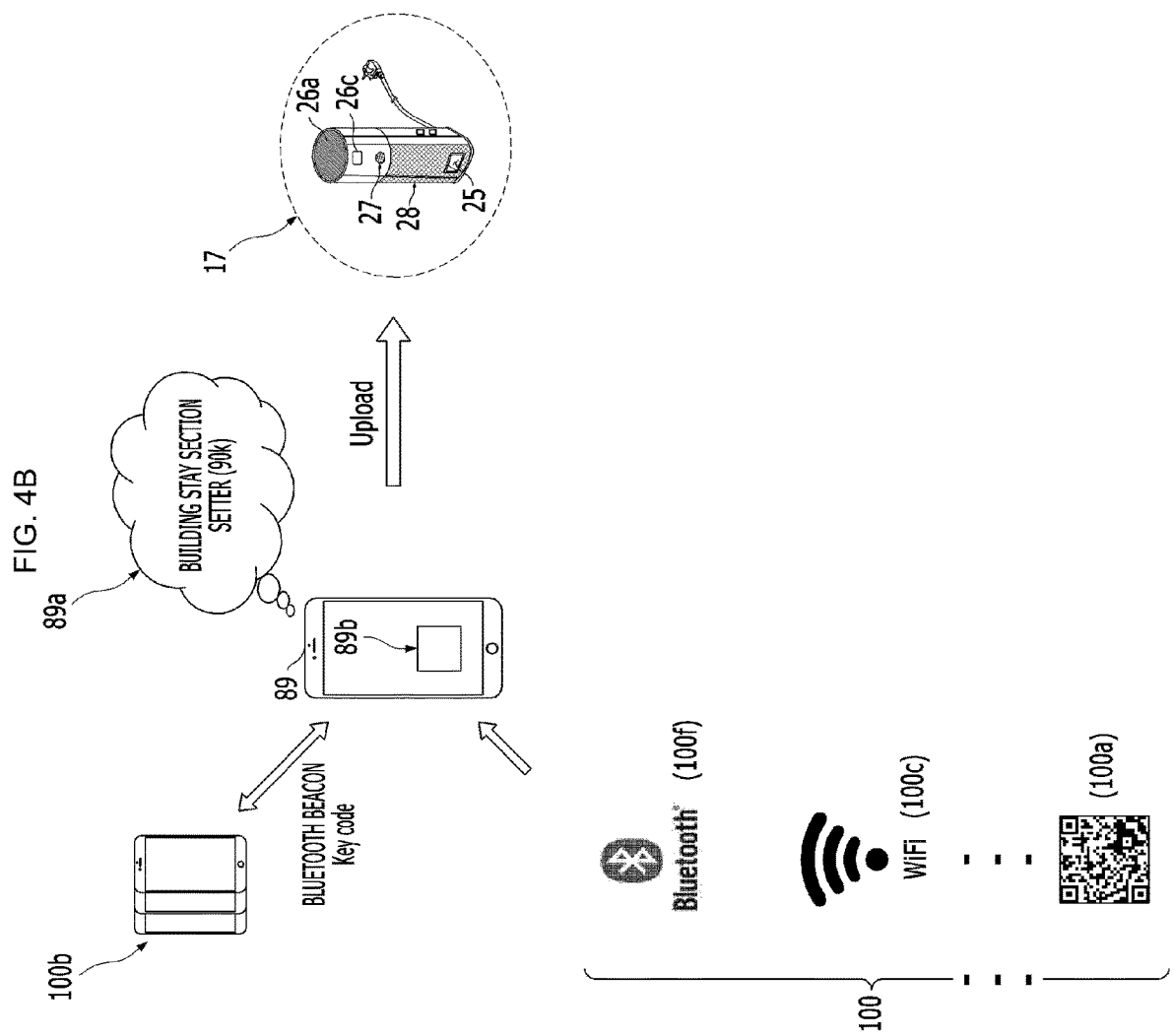

FIG. 5
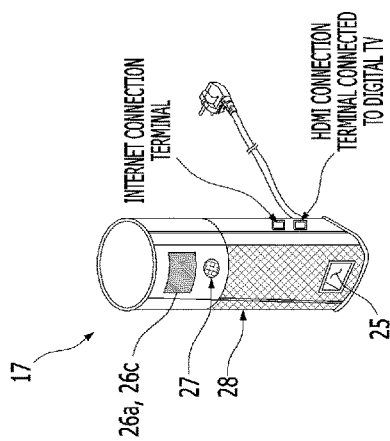
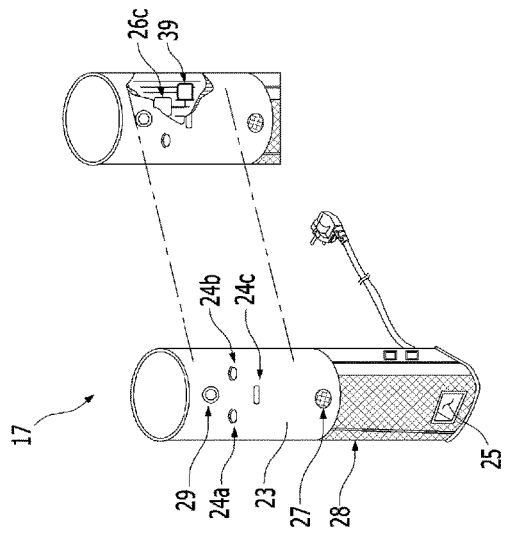

FIG. 6
(a) 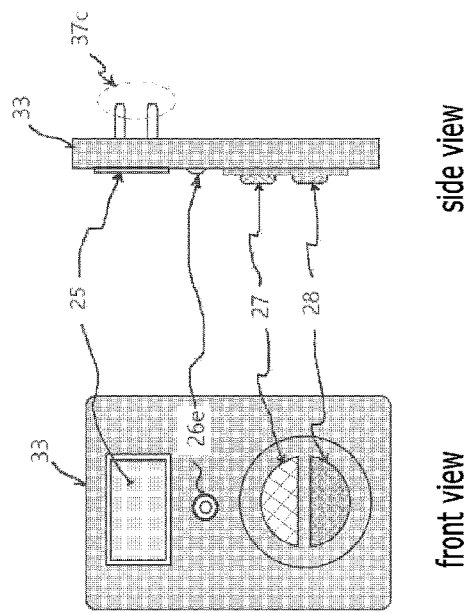
(b) 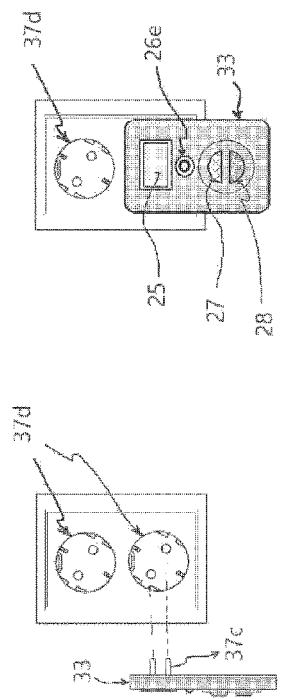

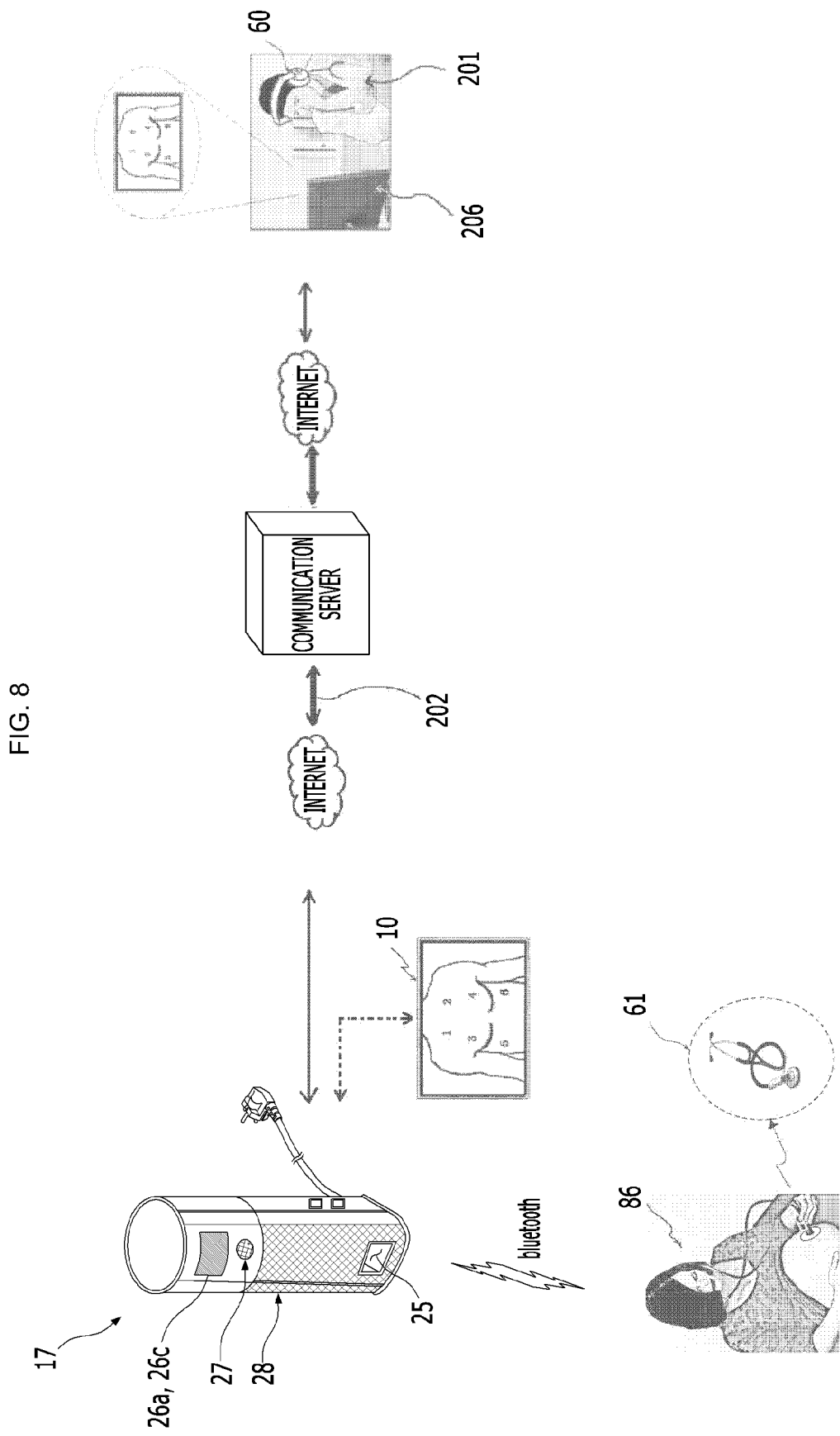

DISTRIBUTED TYPE TRAFFIC LINE TRACING APPARATUS, AND METHOD USING THE SAME

CROSS-REFERENCE TO RELATED APPLICATIONS

This application claims the benefit under 35 USC 119(a) of Korean Patent Application No. 10-2020-0086171 filed on Jul. 13, 2020 in the Korean Intellectual Property Office, the entire disclosure of which is incorporated herein by reference for all purposes.

BACKGROUND

1. Field

The following description relates to a distributed type traffic line tracing apparatus, and method using the same.

2. Description of the Related Art

Recently, as many people receive abundant medical benefits due to the increase in hospital infrastructure along with cutting-edge medical equipment technology, humanity has been promoting more happiness than in the past by extending the lifespan and improving the quality of life.

However, due to the development of transportation, when a global epidemic emerges, it is difficult to prevent the spread of the disease with the existing hospital infrastructure and medical services. In particular, due to the long delay in discovering and quarantining people exposed to an infectious disease, the local community is exposed to the risk of leading to secondary infection and tertiary infection. Moreover, in the case of failing to discover and quarantine a person exposed to the infectious disease, the infection situation becomes worse, and it is difficult to prevent the widespread epidemic.

To solve this problem, Apple and Google recently announced providing an application programming interface (API) related to contact tracing technology that can be used in smartphones. This interface is a method of sending and receiving between smartphones in a short distance a Bluetooth beacon including a specific anonymous code ID (hereinafter referred to as a key code) periodically generated. In this method, exchanged key codes are uploaded to a cloud server, key codes of a smartphone of a person tested positive are checked in response to an occurrence of a confirmed person, close contacts within 14 days having matching key codes are searched and found on the cloud server, a person concerned is informed of this fact, and a notice recommending a test for COVID-19 is sent. Since this technology is based on Bluetooth technology for transmitting and receiving data within 10 meters, it is possible to more accurately identify a contact when compared to the existing base station-based location tracing method that causes an error of 50 to 100 m.

However, in such a method of exchanging key codes between mobile phones based on Bluetooth, it is impossible to find a person with secondary infection by touching an object after a certain period of time after an infected person touches the object. Viruses such as SARS, which have an 80% similarity to the novel COVID-19 virus, are known to persist for 9 days on inanimate surfaces, including metals, glass, and plastics.

In addition, the Chinese and Korean authorities are requiring quick response (QR) code authentication for visitors in order to facilitate tracing of group infections that occur in places where close user contact occurs, such as clubs, motels, and taverns.

In this QR code authentication method, when a specific visitor downloads a QR code through a mobile phone application and enters a business, the downloaded QR code is reported, and mobile phone information is automatically uploaded along with the QR code on a public server, thereby providing an advantage of being able to easily search for visitors of the business by searching the public server for the QR code when a confirmed person occurs in the business in the future. However, since such a QR code is loaded (uploaded) along with personal information and private information on the public server, when the information is leaked to the outside before being destroyed, there is a problem with personal privacy protection. Besides, an individual involved desiring to conceal the fact that the individual has been to a place such as a motel or an entertainment place may refuse QR code authentication. In addition, it is difficult to check the time at which a visitor to the business leaves the business. Thus, when a confirmed person occurs, all people visiting the business on the same day are included in a quarantine candidate pool, resulting in a problem that a suspicious contact pool becomes excessively large.

In addition, in a location tracing method using the global positioning system (GPS) or mobile phone base station, distinguishment in units of buildings is difficult due to poor location tracing accuracy, and there is a high concern that access records of general pedestrians are passed to quarantine authorities and used for monitoring purposes.

The technology behind the present application is disclosed in Korean Laid-Open Patent Publication No. 10-2020-0047457.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a distributed type traffic line tracing apparatus includes a digital communication module installed in a region in a residence of a tracing target person, a traffic line tracing management application, communication connection verifier, a tracing target person traffic line information memory, a memory scheduler, a confirmed person traffic line information memory, a traffic line coincidence determiner, a controller, and control right transferer. The traffic line tracing management application is installed in a mobile phone of the tracing target person. The traffic line tracing management application is configured to store mobile phone location information of the tracing target person provided from a plurality of location information providers in a resident memory of the mobile phone, and wirelessly transmit the mobile phone location information to the digital communication module or a remote server when necessary. The communication connection verifier, resident in the traffic line tracing management application, is configured to verify whether the digital communication module and the mobile phone are connected through short-range communication. The tracing target person traffic line information memory is configured to store traffic line history information of the mobile phone. A memory scheduler is configured to move and store the mobile phone location information stored in the resident memory of the mobile phone in the tracing target person traffic line information memory through wireless connection between the digital communication module and the mobile phone or read traffic line history information of the tracing target person from the remote server to move and store the traffic line history information of the tracing target person in the tracing target person traffic line information memory, and delete content of the remote server after completing the move and the store. The confirmed person traffic line information memory is configured to store traffic line information of a confirmed person provided through the digital communication module. The traffic line coincidence determiner is configured to determine whether there is an overlapping path between a traffic line of the tracing target person and a traffic line of the confirmed person. The controller is configured to select the tracing target person as a quarantining target person when there is an overlapping path between the traffic line and the traffic line of the confirmed person, and drive the digital communication module to transmit information about the selected quarantining target person to a disease management authority terminal. The control right transferer is configured to transfer a control right of the controller to the disease management authority terminal.

The traffic line information of the confirmed person may include any one or any combination of any two or more of pieces of information about a location selected from GPS coordinates on the traffic line of the mobile phone of the confirmed person, a base station accessed by the mobile phone of the confirmed person, a QR code of a visited place of the confirmed person, a key code collected by the mobile phone of the confirmed person, a Bluetooth transmitter ID collected by the mobile phone of the confirmed person, a Wi-Fi ID accessed by the mobile phone of the confirmed person, and a stay period of the confirmed person synchronized with the location.

The traffic line history information of the mobile phone may include any one or any combination of any two or more pieces of information about a location selected from GPS coordinates on the traffic line of the mobile phone, a base station accessed by the mobile phone, a visited place QR code of the tracing target person, a key code collected by the mobile phone, a Bluetooth transmitter ID collected by the mobile phone, a Wi-Fi ID accessed by the mobile phone, and a stay period synchronized with the location.

The traffic line tracing management application may include a stay validity filter configured to exclusively extract, as valid location information, location information about staying in the same place for a predetermined time or more among pieces of location information of the mobile phone provided from the plurality of location information provider, and accumulate and store the location information in the resident memory on the mobile phone.

The plurality of location information provider may include any one or any combination of any two or more of a global positioning system (GPS) providing location data of the mobile phone using an artificial satellite, a Bluetooth transmitter providing a unique ID of the Bluetooth transmitter to the mobile phone, mobile phones of nearby contacts providing key codes by a Bluetooth beacon, an access point (AP) of a wireless LAN providing a Wi-Fi ID to the mobile phone, a black-and-white grid pattern providing a QR code of a visited place, and a base station providing mobile communication location information about connection to the mobile phone.

When a same key code is generated a predetermined number of times or more per hour, the stay validity filter may be further configured to select key codes generated the predetermined number of times or more as valid key code information, and accumulate and store the key codes in the resident memory on the mobile phone.

The traffic line tracing management application may include Wi-Fi switcher configured to force the mobile phone to temporarily switch to a Wi-Fi mode, search for Wi-Fi allowed to communicate with the mobile phone, collect information about a found Wi-Fi ID, and associate and store the Wi-Fi ID with time information synchronized with the Wi-Fi ID in the resident memory on the mobile phone.

The traffic line tracing management application may include Bluetooth switcher configured to force the mobile phone to temporarily switch to a Bluetooth scan mode, search for a Bluetooth transmitter allowed to communicate with the mobile phone, collect information about a found Bluetooth transmitter ID, and associate and store the Bluetooth transmitter ID with time information synchronized with the Bluetooth transmitter ID in the resident memory on the mobile phone.

The traffic line tracing management application may include QR code register, and the QR code register may be configured to determine whether an image captured by a camera of the mobile phone includes QR code information, request fingerprint authentication of the tracing target person from the mobile phone when the image is a QR code, and associate and automatically store the QR code with visit time information in the resident memory on the mobile phone when the tracing target person performs fingerprint authentication.

The traffic line tracing management application may include quarantiner confirmer, and the controller or the disease management authority terminal may provide notification information reporting confirmation of a quarantining target person to the mobile phone proved to be the quarantining target person, the quarantining target person may check the notification information displayed on the mobile phone of the quarantining target person through a fingerprint authentication procedure, and the quarantiner confirmer may confirm the quarantining target person based on a result of performing the fingerprint authentication procedure by the quarantining target person.

The traffic line history information or the mobile phone location information may include a building address expressed by being combined with building information provided by geographic information system (GIS) building integration information.

The QR code register may be characterized in that when fingerprint authentication of the tracing target person is completed, a success message selected from a discount coupon, an advertisement for a visited place, an admission ticket, and a QR code for an admission ticket is displayed on a display window of the mobile phone.

In another general aspect, a distributed type traffic line tracing apparatus having a voice recognition terminal installed in a region in a residence of a tracing target person, the voice recognition terminal includes a digital communication module configured to provide a communication connection between a disease management authority terminal and a mobile phone of the tracing target person; a tracing target person traffic line information memory configured to store traffic line history information of the mobile phone; a memory scheduler configured to read location information of the mobile phone stored in a resident memory on the mobile phone through a wireless connection between the digital communication module and the mobile phone, and move and stores the read location information in the tracing target person traffic line information memory; a confirmed person traffic line information memory configured to store traffic line information of a confirmed person provided through the digital communication module; a traffic line coincidence determiner configured to verify whether there is an overlapping path between a traffic line of the tracing target person and a traffic line of the confirmed person; a controller configured to drive the digital communication module for selecting the tracing target person as a quarantining target person when there is an overlapping path between a traffic line and a traffic line of the confirmed person, and transmit information about the selected quarantining target person to the disease management authority terminal; and control right transferer configured to transfer a control right of the controller to the disease management authority terminal.

The voice recognition terminal may further include a body heat check diagnoser that includes a thermal imaging camera or an infrared temperature sensor configured to measure body heat by detecting heat radiation emitted from a body of the tracing target person, a face recognizer or a fingerprint authenticator configured to recognize the tracing target person, and a body heat determiner configured to measure a maximum temperature value from pixels of an image of the thermal imaging camera corresponding to a face region or measuring a temperature value by the infrared temperature sensor from a forehead part of the face region, thereby determining that the tracing target person is an abnormal body heat suspected subject in a case of an abnormal body heat temperature.

The voice recognition terminal may further include an infrared temperature sensor configured to measure body heat of the tracing target person using infrared rays, a cylindrical display device configured to visually display virtual eyes and mouth to induce correct alignment between a forehead of the tracing target person and the infrared temperature sensor, an image sensor provided on an inside of the cylindrical display device to superimpose and capture an image of the virtual eyes and mouth displayed on the cylindrical display device and an image of eyes and a mouth of the tracing target person from the inside of the cylindrical display device, and alignment information provider configured to provide feedback information on an alignment position to the tracing target person by determining a superimposed image generated based on the image of the virtual eyes and mouth and the image of the eyes and mouth of the tracing target person, and when superimposed image alignment generated based on the image of the virtual eyes and mouth and the image of the eyes and mouth of the tracing target person is included within a predetermined range, the infrared temperature sensor measures the body heat from the forehead of the tracing target person.

The mobile phone may include residence departure detector configured to report suspected residence departure to the disease management authority terminal when the quarantining target person left a residence for a predetermined time or more.

The residence departure detector may include a mobile phone dormancy checker configured to check a frequency of shaking of the mobile phone according to a walking movement of a quarantiner and a frequency of using touch of a mobile phone touch pad of the quarantiner, and check a dormant state of the mobile phone when movement information of the quarantiner is not collected from the mobile phone, and a first virtual phone bell generator and a second virtual phone bell generator configured to generate a virtual phone bell sound in a mobile phone of the quarantiner and a speaker when it is determined by the mobile phone dormancy checker of the tracing target person that the mobile phone of the quarantiner is in the dormant state, and when the quarantiner does not receive a call even though the virtual phone bell sound is output a predetermined number of times or more through the mobile phone of the quarantiner and the speaker during the dormant state of the mobile phone, the residence departure detector may be further configured to determine that the quarantiner has left a residence without the mobile phone, and report quarantiner departure to the disease management authority terminal.

The voice recognition terminal may further include residence departure detector. The residence departure detector may include living organism signal collector including at least one of a thermal imaging camera configured to determine whether the quarantiner is present in a given space by observing an image change in a thermal image, an image sensor for knowing presence or absence of movement of the quarantiner by checking an image variation, an infrared human body detection sensor that detects presence or absence of movement of the quarantiner by checking a fluctuation of infrared rays emitted from a body of the quarantiner, and a microphone configured to determine whether breathing sound or living sound of the quarantiner is present, an energy fluctuation curve calculator configured to calculate a time-dependent energy fluctuation from a signal obtained from the living organism signal collector, a short-range communication network connection checker that verifies whether short-range wireless communication connection to the mobile device of the quarantiner is performed by the digital communication module, a quarantiner dormancy checker configured to determine that the quarantiner is in a quarantiner dormant state in which there is no movement of the quarantiner when it is determined by the short-range communication network connection checker that the mobile device of the quarantiner is not in the residence or the energy fluctuation continues at a reference value or less for a predetermined time period or more, and a second virtual phone bell generator configured to generate a virtual phone bell sound in the speaker when the quarantiner dormancy checker determines that the quarantiner is in the dormant state, when the quarantiner does not receive a call even though the virtual phone bell sound is output a predetermined number of times or more through the mobile phone of the quarantiner and the speaker during the dormant state of the quarantiner, the residence departure detector is further configured to determine that the quarantiner has left the residence, and the controller reports quarantiner departure to the disease management authority terminal through the digital communication module.

The residence departure detector may further include a fingerprint authenticator configured to perform a fingerprint authentication procedure, and the fingerprint authenticator may perform identification through the fingerprint authentication procedure for reception of the call.

The residence departure detector may include an information collection adapter connected to the digital communication module based on Internet of Things and installed for each of individual spaces, and the information collection adapter may include a speaker, a microphone, an infrared human body detection sensor, an infrared temperature sensor, and a fingerprint authenticator.

The residence departure detector may further include a fingerprint authenticator configured to perform a fingerprint authentication procedure, and the fingerprint authenticator may perform identification through the fingerprint authentication procedure for reception of the call.

The residence departure detector may include an information collection adapter connected to the digital communication module based on Internet of Things and installed for each of individual spaces, and the information collection adapter may include a speaker, a microphone, an infrared human body detection sensor, an infrared temperature sensor, and a fingerprint authenticator.

The voice recognition terminal may include the digital communication module, a medical data receptor configured to receive medical data measured from a plurality of medical devices by short-range communication connection to medical devices, and an artificial neural network subjected to deep learning in advance by pieces of medical data for training, and the artificial neural network subjected to deep learning may be configured to analyze the medical data received by the medical data receptor to automatically determine presence or absence of a disease of a patient and a risk of the disease.

The mobile phone may include building stay section setter configured to trace and check location information provided from the location information provider to calculate a stay section in which the mobile phone stayed at a corresponding building, and the mobile phone reads a plurality of key codes acquired from mobile phones of nearby contacts during a building stay section through wireless communication connection with the voice recognition terminal at an end of stay of the corresponding building calculated by the building stay section setter, and moves and stores the read key codes in the tracing target person traffic line information memory of the voice recognition terminal.

Other features and aspects will be apparent from the following detailed description, the drawings, and the claims.

BRIEF DESCRIPTION OF THE DRAWINGS

FIG. 4A is a diagram schematically illustrating an example of QR code registerapparatus of the distributed type traffic line tracing apparatus according to the embodiment of the present application, in which a QR address is stored in a memory residing on a mobile phone by converting a QR code into a corresponding visited place address.

FIG. 4B is a diagram schematically illustrating an example in which key codes provided from mobile phones of nearby contacts by Bluetooth beacons of the distributed type traffic line tracing apparatus according to the embodiment of the present application are stored in a resident memory on a mobile phone of a tracing target person, and the key codes stored in the resident memory are moved and stored in a voice recognition terminal through a wireless connection with the voice recognition terminal.

FIG. 5 is a diagram schematically illustrating a voice recognition terminal having a built-in Internet router of the distributed type traffic line tracing apparatus according to the embodiment of the present application.

FIG. 6 is an example schematically illustrating an information collection adapter of the distributed type traffic line tracing apparatus according to the embodiment of the present application provided with connection to a digital communication module through Bluetooth, Wi-Fi or Internet of Things connection for each individual living space in a residence.

FIG. 8 is a diagram schematically illustrating an example of a telemedicine diagnosis in which a doctor remotely checks a health condition of a fetus using the distributed type traffic line tracing apparatus according to the embodiment of the present application and a stethoscope among the plurality of medical devices.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
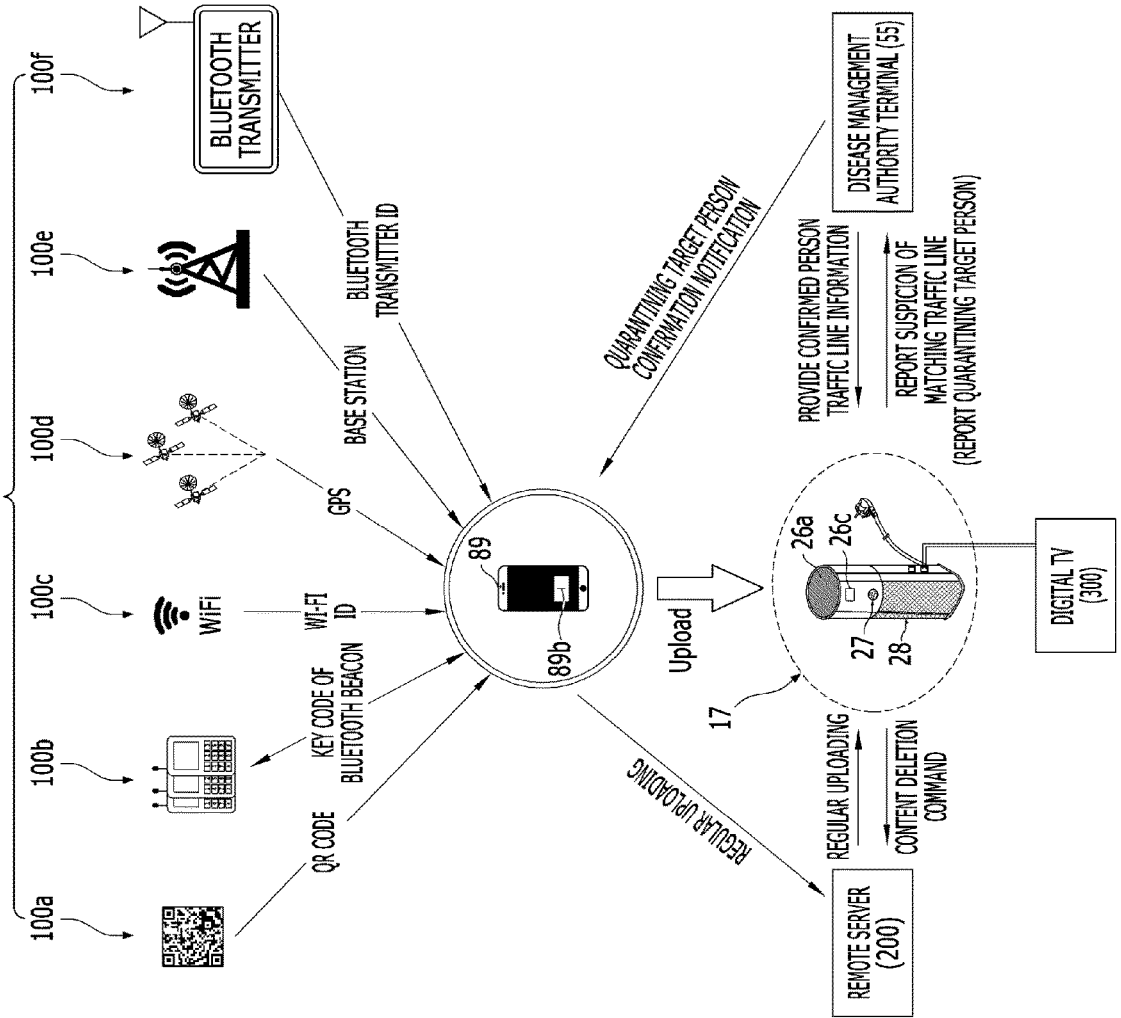
FIG. 1 is a diagram schematically illustrating an example in which a distributed type traffic line tracing apparatus according to an embodiment of the present application is converted into a voice recognition terminal that provides various contents to a digital TV through high-speed Internet connection and controls the digital TV by a voice command.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The features of the examples described herein may be combined in various ways as will be apparent after an understanding of the disclosure of this application. Further, although the examples described herein have a variety of configurations, other configurations are possible as will be apparent after an understanding of the disclosure of this application.

Meanwhile, the present disclosure is a continuation of a ceiling-type artificial intelligence health monitoring apparatus and a telemedicine diagnosis method using the same (application number: 10-2020-0055019) and a quarantiner monitoring apparatus and a method using the same (application number: 10-2020-0071282).

The present disclosure provides a distributed type apparatus and method allowing a traffic line tracing apparatus of the present disclosure, which is personally installed in a residence of a tracing target person, to automatically verify whether or not a traffic line of a confirmed person is matched and automatically report a result to a disease management authority only when the confirmed person is matched in an emergency situation such as an infectious disease pandemic, so that a quarantining target person is automatically found early while protecting the a privacy of an individual much more when compared to a centralized type, thereby rapidly establishing an infectious disease management system for patients with suspected diseases and efficiently managing the patients from the spread of infectious diseases. In addition, the present disclosure can be used for tracing a location of a criminal and identifying an alibi.

The present disclosure provides the following advantage. For example, when an infectious disease spread occurs in a specific location, the national authority or the disease management authority provides information about a traffic line and a stay period of a confirmed person to a traffic line tracing apparatus of the present disclosure so that the traffic line tracing apparatus determines whether a traffic line of a tracing target person overlaps the traffic line of the confirmed person during the stay period. Further, only when the traffic line of the tracing target person overlaps the provided traffic line of the confirmed person, the traffic line tracing apparatus is allowed to automatically report the information to the disease management authority so that the tracing target person is automatically confirmed as a quarantining target person. In this way, not only the spread of the infectious disease can be promptly suppressed at an early stage, but also quarantiners are automatically selected and quarantined without personal privacy exposed to the outside. The tracing target person selected as a quarantiner has a quarantine time for a predetermined period (for example, 14 days).

A distributed type traffic line tracing apparatus of the present disclosure is a personal property installed in a residence of a tracing target person, and provides the following advantages. When compared to a conventional centralized location tracing apparatus, it is significantly unlikely that a large amount of private life will be leaked to the outside at once so that personal privacy is well protected. Besides, since the tracing apparatus is distributed as a personal property device, no load is applied due to a location tracing operation when compared to the centralized type.

In addition, the distributed type traffic line tracing apparatus of the present disclosure provides the following advantages. A person whose traffic line matches a traffic line of a confirmed person is automatically declared as a quarantiner and quarantined in a residence. Besides, immediately after the declaration of quarantine, the apparatus enters into a departure monitoring system that monitors whether or not the quarantiner leaves the residence, and medical consultation with the quarantiner can be conducted by telemedicine treatment, so that it is possible to prevent cross-infection of medical staff and shortage of ward.

Accordingly, the present disclosure provides a one-stop solution allowing traffic line tracing, quarantiner finding, quarantiner departure monitoring, and telemedicine treatment at once.

The distributed type traffic line tracing apparatus of the present disclosure can most optimally monitor a tracing target person at all times when the apparatus is on the ceiling, and thus it is preferable that the apparatus of the present disclosure has a structure incorporated into a ceiling type air conditioner or a ceiling type lighting fixture.

Preferably, another aspect of the distributed type traffic line tracing apparatus of the present disclosure provides various contents to a digital TV through high-speed Internet connection and is more preferably merged with a voice recognition terminal that controls the digital TV by a voice command.

However, the technical problems to be achieved by the embodiments of the present application are not limited to the technical problems as described above, and other technical problems may exist.

Hereinafter, preferred embodiments of the present disclosure will be described in detail with reference to the accompanying drawings.

Hereinafter, a distributed type traffic line tracing apparatus (not illustrated) of the present disclosure may be referred to as a traffic line tracing apparatus (not illustrated) for convenience of description, and the distributed type traffic line tracing apparatus (not illustrated) and the traffic line tracing apparatus (not illustrated) may be interchangeably used. In addition, a mobile phone of the present disclosure can be used as a term collectively referred to as (mixed with) a mobile terminal including a tablet PC. In the present disclosure, a tracing target person may refer to a user who resides in a residence in which the traffic line tracing apparatus (not illustrated) is installed and registered a Wi-Fi or Bluetooth connection to allow wireless communication between the traffic line tracing apparatus (not illustrated) and a mobile phone of the user. In addition, a mobile phone corresponding to reference symbol 89 of the present disclosure may include all of the mobile phone of the tracing target person, a mobile phone of a quarantining target person, and a mobile phone of a confirmed person.

In the present disclosure, a base station is collectively referred to as a term including a repeater for supporting a smooth communication network connection of the mobile phone. In addition, in the present disclosure, Wi-Fi refers to all means of wireless Internet. In addition, in the present disclosure, a Wi-Fi ID collectively refers to a service set identifier (SSID) or a media access control address (MAC) address. The SSID is a unique ID name assigned to the Internet routers currently installed in the vicinity, and is a value set in the Internet router. In the present disclosure, the confirmed person collectively refers to those reliably diagnosed with a type or condition of a disease by means of disease measurement.

FIG. 1 is a diagram schematically illustrating an example in which the traffic line tracing apparatus of the present application is converted into a voice recognition terminal 17 that provides various contents to a digital TV 300 through high-speed Internet connection and controls the digital TV 300 by a voice command.

Illustratively, FIG. 1 may illustrate an example in which a traffic line tracing management application (not illustrated) installed (residing) in the form of an application on a mobile phone 89 of a tracing target person accumulates and stores location information of the mobile phone 89 of the tracing target person provided from a plurality of location information provider 100 in a resident memory 89b on the mobile phone of the tracing target person, and, whenever necessary, wirelessly transmits the content of the resident memory 89b to the voice recognition terminal 17 through short-range communication to upload the content or wirelessly transmits mobile phone location information accumulated and stored in the resident memory 89b to a remote server 200 on a regular basis.

According to an embodiment of the present application, the plurality of location information provider 100 may include at least any one of a GPS 100d providing location data of the mobile phone 89 using an artificial satellite, a Bluetooth transmitter 100f providing a unique ID of the Bluetooth transmitter to the mobile phone 89, peripheral mobile phones 100b providing a key code by a Bluetooth beacon, an AP 100c of a wireless LAN providing a Wi-Fi ID to the mobile phone 89, a black-and-white grid pattern 100a providing a QR code of a visited place, and a base station (repeater) 100e providing mobile communication location information about connection to the mobile phone 89 of the tracing target person.

Today, the means is widely used in a navigator that shows a current location on a map by checking an exact location of a current place using the GPS and then comparing the location with map information stored by the geographic information system (GIS). A method using GPS satellite signals is a method of receiving signals from at least two or three or more GPS satellites and measuring a location on a ground surface using a difference in the reception time. However, there is a disadvantage in that GPS satellite signals are not well captured indoors, and thus it is not easy to accurately measure the location in a large building.

Meanwhile, a building address, which is expressed by being combined with building information based on GIS building integration information, is preferred for traffic line information or mobile phone location information. The GIS building integration information is information that displays building information together with map information, and refers to space (land)-based building integration information built by integrating building space information and building ledger attribute information in units of buildings based on cadastral map information.

As an example, it is preferable that the traffic line tracing management application installed (resident) on the mobile phone of the tracing target person identifies location data of the mobile phone by GPS location data using satellites or mobile phone access base station (repeater)-based geographic information, and stores synchronized time information together with the identified location data in the memory 89b residing on the mobile phone of the tracing target person.

In addition, the plurality of location information provider 100 is characterized by including at least any one of the GPS 100d providing the location data of the mobile phone using the artificial satellite, the Bluetooth transmitter providing the unique ID of the Bluetooth transmitter to the mobile phone, mobile phones of nearby contacts providing key codes by a Bluetooth beacon, the AP of the wireless LAN providing the Wi-Fi ID to the mobile phone, the black-and-white grid pattern providing the QR code of the visited place, and the base station (repeater) providing the mobile communication location information about connection to the mobile phone. In addition, it is preferable that the traffic line tracing management application installed (resident) on the mobile phone of the tracing target person identifies location data of the mobile phone by GPS location data using satellites or mobile phone access base station (repeater)-based geographic information, and stores the location data and time information synchronized with the location data together in the memory residing on the mobile phone of the tracing target person.

In addition, geographic information based on a base station of a telecommunication company is used to identify the location of the mobile phone by a communication network formed by WIFI, 3G, 5G, and LTE networks, and it is possible to use any one of a method of finding a location by radio waves of a mobile communication base station, a cell tracing method, or a method in which three or more base stations transmit radio waves to a terminal to determine a location based on a time difference between return radio waves.

In addition, referring to FIG. 1, the voice recognition terminal 17 may periodically read traffic line history information of the tracing target person from the remote server 200 to move and store the traffic line history information of the tracing target person in a storage space, and delete recorded content related to the traffic line history information of the tracing target person stored in the corresponding remote server 200 after completion of moving and storing. In addition, in another aspect of the voice recognition terminal 17, it is preferable that the voice recognition terminal 17 reads traffic line history information of the tracing target person from the remote server 200 to move and store the traffic line history information in a storage space without delay each time the mobile phone location information accumulated and stored in the resident memory 89b is transmitted to the remote server 200, and immediately deletes and discards recorded content related to the traffic line history information of the tracing target person stored in the corresponding remote server 200 after completion of moving and storing. In this case, a stay period in which the traffic line history information of the tracing target person is left in the remote server 200 can be minimized, so that leakage of personal information can be prevented.

In addition, in another aspect of the voice recognition terminal 17, it is more preferable to use a mobile phone-to-voice terminal communication mode in which the mobile phone location information accumulated and stored in the resident memory 89b is moved and stored in the storage space of the voice recognition terminal 17 by a direct wireless communication connection between the mobile phone 89 of the tracing target person and the voice terminal 17 without using the remote server 200. In this case, the voice recognition terminal 17 moves and stores the mobile phone location information stored on the resident memory 89b in the storage space of the voice recognition terminal 17 by wireless communication connection between the mobile phone 89 and the voice recognition terminal 17. It is preferable that the mobile phone location information stored in the corresponding resident memory 89b is automatically deleted after completion of moving and storing.

The mobile phone-to-voice terminal communication mode provides an advantage of completely preventing personal information leakage since the traffic line history information of the tracing target person stored in the resident memory 89b can be directly stored in the storage space of the voice recognition terminal 17 without passing through the remote server 200.

It is preferable that the mobile phone-to-voice terminal communication mode is regularly activated when the mobile phone of the tracing target person deviates from a normal activity range of the tracing target person (for example, due to a business trip, a vacation, etc.).

The tracing target person can set an initial value of the activity range of the tracing target person through a traffic line tracing management application 89a, and it is preferable that the activity range is varied thereafter according to a life pattern of the tracing target person based on information provided from the plurality of location information provider 100.

For example, the initial value of the activity range is preferably 50 Km, and a subsequent activity range may be set as an average of lower limit activity ranges for 4 days among activity ranges of the mobile phone of the tracing target person for the last 7 days.

In addition, a disease management authority terminal 55 may provide traffic line information of a confirmed person to the voice recognition terminal 17 when the confirmed person occurs, and the voice recognition terminal 17 may determine whether or not the traffic line of the confirmed person coincides with the traffic line of the tracing target person and automatically report to the disease management authority terminal 55 that the tracing target person is a quarantining target person when the traffic lines coincide with each other.

In addition, the disease management authority may closely analyze the traffic line of the tracing target person reported as a quarantiner, and then provide a text message (notification information), which reports that the tracing target person is confirmed as a quarantining target person, to the mobile phone 89 of the tracing target person proved to be a quarantining target person through the disease management authority terminal 55 when it is certain that the traffic line coincides with the traffic line of the confirmed person.

Figure 2:
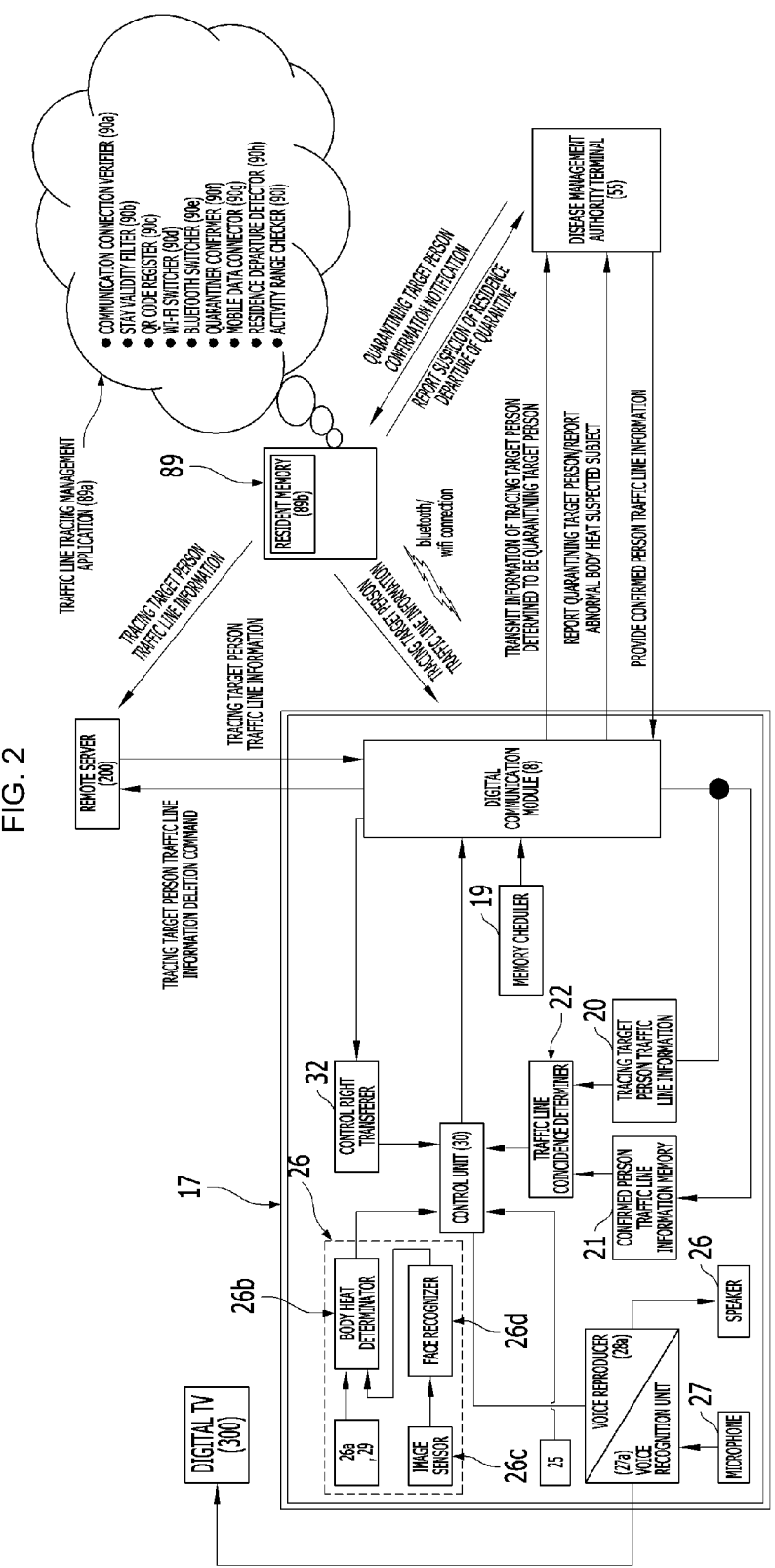
FIG. 2 is a diagram schematically illustrating another example in which the distributed type traffic line tracing apparatus according to the embodiment of the present application is converted into the voice recognition terminal that provides various contents to the digital TV through high-speed Internet connection and controls the digital TV by the voice command.

FIG. 2 is a diagram schematically illustrating another example in which the distributed type traffic line tracing apparatus according to the embodiment of the present application is converted into the voice recognition terminal 17 that provides various contents to the digital TV 300 through high-speed Internet connection and controls the digital TV 300 by the voice command.

Referring to FIG. 2, the voice terminal 17 may be provided in a region within a residence of the tracing target person. In addition, the voice recognition terminal 17 may include a digital communication module 8, a tracing target person traffic line information memory 20, a memory scheduler 19, a confirmed person traffic line information memory 21, a traffic line coincidence determiner 22, a controller 30, and control right transferer 32.

According to the embodiment of the present application, the digital communication module 8 may provide communication with the disease management authority terminal 55, provide a wireless communication connection with the mobile phone 89 of the tracing target person, or provide a short-range communication (Bluetooth or Wi-Fi) connection with the mobile phone 89 of the tracing target person.

In addition, the tracing target person traffic line information memory 20 may store traffic line history information of the mobile phone 89 of the tracing target person.

In addition, the memory scheduler 19 may read the mobile phone location information of the tracing target person accumulated and stored in the resident memory 89b on the mobile phone of the tracing target person through connection with the digital communication module 8, and move and store the information in the tracing target person traffic line information memory 20. In addition, the memory scheduler 19 may drive the digital communication module 8 to read traffic line history information of the tracing target person from the remote server 200 regularly (every preset time), move and store the traffic line history information of the tracing target person in the tracing target person traffic line information memory 20, and delete content of the remote server 200 after completion of moving and storing.

In addition, the confirmed person traffic line information memory 21 may store traffic line information of the confirmed person provided from the disease management authority terminal 55 through the digital communication module 8.

In addition, the traffic line coincidence determiner 22 may compare traffic line information (content) of the confirmed person traffic line information memory 21 with traffic line information (content) of the tracing target person traffic line information memory 20 to determine whether the traffic line of the tracing target person coincides with the traffic line of the confirmed person. In other words, the traffic line coincidence determiner 22 may compare confirmed person traffic line information with tracing target person traffic line information to determine whether there is a path in which the traffic line of the tracing target person overlaps the traffic line of the confirmed person.

In addition, the traffic line coincidence determiner 22 may compare a building address stored in the confirmed person traffic line information memory with a building address stored in the tracing target person traffic line information memory, and when stay periods on the traffic lines overlap each other, the traffic line coincidence determiner 22 may determine that the traffic line of the tracing target person coincides with the traffic line of the confirmed person and classify the tracing target person as a quarantining target person.

Meanwhile, in the case of an outbreak of an infectious disease pandemic, the disease management authority terminal 55 may provide traffic line information of the confirmed person to the confirmed person traffic line information memory 21 through the digital communication module 8. In this instance, when the traffic line of the tracing target person overlaps the traffic line of the confirmed person, the controller 30 may drive the digital communication module 8 to select the tracing target person as a quarantining target person and perform automatic transmission to the disease management authority terminal 55. In addition, the control right transferer 32 may transfer a control right of the controller 30 to the disease management authority terminal 55.

According to the embodiment of the present application, when the tracing target person is determined to be a quarantining target person, the controller 30 may drive the digital communication module 8 to transmit and report information (for example, traffic line history information, residence address, name, age, gender, mobile phone number, e-mail address, resident registration number, etc. stored in the tracing target person traffic line information memory) of the tracing target person determined to be the quarantining target person to the disease management authority terminal 55. In this instance, the disease management authority may closely analyze the reported traffic line of the tracing target person, and then when coincidence with the traffic line of the confirmed person is certain, the disease management authority may transmit (provide) notification (information) of confirmation of the quarantining target person to the mobile phone 89 of the tracing target person through the disease management authority terminal 55.

In addition, the memory scheduler 19 is characterized by driving the digital communication module 8 to read traffic line information of the tracing target person from the remote server 200 at predetermined time intervals (regular time intervals), moving and storing the information in the tracing target person traffic line information memory 20, and then immediately deleting the corresponding recorded content of the remote server 200 to protect personal privacy.

As an example, a regular (every predetermined time) reading time interval of the remote server 200 is preferably 2 to 6 hours. In this case, a time interval for deleting the recorded content of the remote server 200 is also 2 to 6 hours, so it is possible to minimize a time during which personal information remains on the remote server 200.

Reference symbol 89*a* denotes the traffic line tracing management application which resides (is installed) in the form of an application on the mobile phone 89 of the tracing target person, and accumulates and stores location information of the mobile phone 89 of the tracing target person provided from the plurality of location information provider 100 in the resident memory 89*b* on the mobile phone, and wirelessly transmits content of the resident memory 89*b* to the digital communication module 8 when necessary or wirelessly transmits mobile phone location information (traffic line information of the tracing target person) accumulated and stored in the resident memory 89*b* to the remote server 200 on a regular basis.

According to the embodiment of the present application, the traffic line tracing management application 89*a* may include communication connection verifier 90*a*, a stay validity filter 90*b*, QR code register 90*c*, Wi-Fi switcher 90*d*, Bluetooth switcher 90*e*, quarantiner confirmer 90*f*, activity range checker 90*i*, and mobile data connector 90*g*.

In addition, the communication connection verifier 90*a* is preferably installed (resident) in the traffic line tracing management application (89*a*), and preferably transmits location information of the mobile phone accumulated and stored in the resident memory 89*b* on the mobile phone to the digital communication module 8 each time the tracing target person leaves the residence and then re-enters the residence.

In addition, it is preferable that the communication connection verifier 90*a* determines that communication is disconnected when the Bluetooth and Wi-Fi connection strength between the mobile phone and the digital communication module is less than or equal to a predetermined value, and determines that the tracing target person re-entered the residence when the connection signal strength becomes stronger than the reference strength after a predetermined time elapses.

In addition, the communication connection verifier 90*a* may further include mobile data suspender for temporarily suspending the use of mobile data of the mobile phone of the tracing target person, so that the use of mobile data is suspended during a period in which whether the tracing target person left the residence is verified. Then, the communication connection verifier 90*a* may check Wi-Fi connection strength information between the mobile phone of the tracing target person and the digital communication module, and determine that the tracing target person left the residence when the Wi-Fi connection signal strength is weakened below a reference value or a connection attempt fails.

In addition, the communication connection verifier 90*a* is characterized by determining that re-entry into the residence is performed when the Wi-Fi connection signal strength becomes stronger than the reference value after the Wi-Fi connection signal strength becomes weaker than the reference value or the connection attempt fails.

In addition, the communication connection verifier 90*a* may detect a latest (new) Bluetooth beacon signal or a latest (new) Wi-Fi ID from around the mobile phone 89.

In addition, the activity range checker 90*i* is preferably installed (resident) in the traffic line tracing management application 89*a*, and preferably transmits the location information of the mobile phone accumulated and stored in the resident memory 89*b* on the mobile phone to the digital communication module 8 for a predetermined time (regularly) through the mobile phone-to-voice terminal communication mode when it is determined that the mobile phone 89 of the tracing target person is deviated from a designated activity range.

In addition, when the tracing target person captures a picture of a QR code of a visited place using a camera of the mobile phone 89 of the tracing target person, the QR code registrar 90*c* may associate the captured QR code with visit time information and automatically store in the memory 89*b* resident on the mobile phone.

In addition, it is preferable that the QR code register 90*c* determines whether or not an image captured by the mobile phone camera is a QR code, and in the case of a QR code image, the QR code picture of the visited place is automatically captured in response to fingerprint authentication of the tracing target person, and visit time information along with the QR code is automatically stored in the memory residing on the mobile phone. The QR code picture is automatically captured by fingerprint authentication, and thus security can be maintained.

In addition, the QR code register 90c more preferably converts the QR code into a corresponding visited place address (hereinafter referred to as a QR address) so that the QR address is stored in the memory resident in the mobile phone. To this end, the QR code register is characterized by sending the QR code to a responsible server (for example, a QR code-to-address conversion server) that converts the QR code into an address and receiving a QR address decoded to a visited place address in return.

In addition, the QR code register 90c is characterized in that, when the QR code or QR address is stored in the memory residing on the mobile phone, a success message indicating successful registration of a barcode or QR code permitting access to a visited place is displayed on a mobile phone screen.

In addition, the QR code register 90c prefers a building address expressed in combination with building information based on GIS building integration information, which allows conversion of the QR code into a building address in units of buildings or building floors.

According to the embodiment of the present application, Wi-Fi ID information is preferably a building address expressed in combination with building information based on GIS building integration information. In this way, the Wi-Fi ID information can be converted into a building address in units of buildings or building floors.

In addition, Bluetooth transmitter ID information is preferably a building address expressed in combination with building information based on GIS building integration information. In this way, the Bluetooth ID information can be converted into a building address in units of buildings or building floors.

In addition, when the same Wi-Fi ID is generated a predetermined number of times or more per hour, the stay validity filter 90b may select Wi-Fi ID codes generated the predetermined number of times or more as valid Wi-Fi ID information, and accumulate and store the Wi-Fi ID codes in the resident memory 21 of the mobile phone of the tracing target person.

In addition, the traffic line tracing management application 89a may include Wi-Fi switcher for forcibly switching the mobile phone to a Wi-Fi mode to search for Wi-Fi (in the vicinity) enabling communication with the mobile phone of the tracing target person, and collecting found Wi-Fi ID information to store the corresponding Wi-Fi ID and synchronized time information together in the memory residing on the mobile phone. In general, since the Wi-Fi ID is different for each floor of a building, when a nearby Wi-Fi ID is stored in a memory residing on the mobile phone, it is easy to trace the location of the mobile phone on a multistory building.

In addition, the SSID of the present disclosure is preferably a Wi-Fi ID including a building address and a floor number at a point where a Wi-Fi router is installed, and the traffic line tracing management application preferably receives a beacon signal from a Wi-Fi access point that periodically transmits the SSID, parses the received beacon signal, and identifies the current building address and floor number from the SSID.

In addition, a Bluetooth ID of the present disclosure is preferably an ID including a building address and a floor number at a point where a Bluetooth transmitter is installed, and the traffic line tracing management application preferably receives a beacon signal from a Wi-Fi access point that periodically transmits the Bluetooth ID, parses the received beacon signal, and identifies the current building address and floor number from the Bluetooth ID.

In addition, the traffic line tracing management application 89a is characterized by collecting key codes periodically generated from mobile phones around the tracing target person and storing the corresponding key codes and time information synchronized with the key codes together in the memory residing on the mobile phone. The key code of the present disclosure is stored in the resident memory on the mobile phone instead of being stored on the cloud server, and thus personal privacy can be protected.

The quarantiner confirmer 90f according to the embodiment of the present application may complete a quarantining target person confirmation notification procedure by the quarantining target person browsing a notice reporting confirmation of the quarantining target person through a fingerprint authentication procedure on the mobile phone when the controller 30 or the disease management authority terminal 55 transmits the notice to the mobile phone 89 of the tracing target person determined to be the quarantining target person. The notice preferably includes a requirement to be observed by the quarantiner.

According to the embodiment of the present application, the mobile data connector 90g may forcefully activate the use of the mobile data of the mobile phone of the tracing target person. The mobile data connector 90g is characterized by forcibly activating the use of the mobile data of the mobile phone during a period for determining a current location of the mobile phone and then identifying location information of the mobile phone to store the location information on the mobile phone or transmit the location information to the remote server. The mobile data suspender (not illustrated) preferably verifies whether the tracing target person leaves the residence by being activated (executed) at certain time intervals.

The mobile data connector 90g preferably identifies the location information of the mobile phone of the tracing target person by being activated (executed) at certain time intervals.

In addition, the mobile data connector 90g preferably returns to an original mobile data usage state of the mobile phone after checking the location information of the mobile phone.

Meanwhile, the mobile data suspender (not illustrated) preferably returns to the original mobile data usage state of the mobile phone after completing checking whether communication is connected or not.

Referring to FIG. 2, reference symbol 26 may denote a body heat check diagnoser 26 for determining whether the tracing target person is a person suspected of being infected with a disease by measuring body heat of the tracing target person.

According to the embodiment of the present application, the body heat check diagnoser 26 may include a thermal imaging camera 26a, an infrared temperature sensor 29, an image sensor 26c, a face recognizer 26d, and a body heat determiner 26b.

In addition, the thermal imaging camera 26a or the infrared temperature sensor 29 may measure body heat by detecting heat radiation emitted from a body of the tracing target person.

In addition, the image sensor 26c may acquire a body image of the tracing target person.

In addition, the face recognizer 26d may compare an image of the image sensor 26c with a previously registered face database (not illustrated) of the tracing target person to recognize a person of a corresponding face or a face region.

In addition, the body heat determiner 26b may measure a maximum temperature value from pixels corresponding to the face region in the image acquired from the thermal imaging camera 26a. In addition, the body heat determiner 26b may analyze a temperature value measured from a forehead part of the face region using the infrared temperature sensor 29 to determine that the tracing target person is an abnormal body heat suspected subject in the case of an abnormal body heat temperature.

As an example, the infrared temperature sensor 29 may be provided at a distance of 3 cm to 5 cm from a forehead of a subject (user) to perform measurement through an infrared sensor.

Meanwhile, the body heat diagnoser 26 may be activated after performing identity authentication by verifying whether or not a fingerprint of the subject matches a fingerprint of the tracing target person pre-registered by a fingerprint authenticator 2 (25).

In addition, the body heat determiner 26b may presume (determine) that the tracing target person is the abnormal body heat suspected subject when the body heat of the tracing target person is 37.5 degrees or higher.

In addition, when the body heat determiner 26b presumes (determines) that the tracing target person is the abnormal body heat suspected subject, the controller 30 may drive the digital communication module 8 to transmit (report) the corresponding information to the disease management authority terminal 55.

When the tracing target person is determined to be the abnormal body heat suspected subject, content (information) transmitted from the controller 30 to the disease management authority terminal 55 may include information (for example, body heat temperature, address of residence, name, age, gender, mobile phone number, school information for students, etc.) of the tracing target person matched in the authentication process of the fingerprint authenticator 2 (25).

According to the embodiment of the present application, the voice recognition terminal 17 may include the digital communication module 8, the confirmed person traffic line information memory 21, the tracing target person traffic line information memory 20, the traffic line coincidence determiner 22, the memory scheduler 19, the control right transferer 32, the controller 30, and the body heat check diagnoser 26.

The voice recognition terminal 17 may provide various contents to the digital TV 300 through a high-speed Internet connection. The voice recognition terminal 17 may include a voice recognizer 27a and a voice reproducer 28a, control the digital TV 300 by voice commands collected through a microphone 27, and receive voice feedback through a speaker 28.

In addition, the traffic line tracing management application 89a may include residence departure detector 1 (90h) that reports departure of the quarantiner to the disease management authority terminal 55 when the quarantiner leaves the residence for a predetermined time or more.

According to the embodiment of the present application, the memory scheduler 19 may be characterized by reading the location information of the mobile phone 89 of the tracing target person accumulated and stored in the resident memory 89b on the mobile phone by short-range communication connection (Wi-Fi or Bluetooth) between the mobile phone 89 of the tracing target person and the digital communication module 8 and moving and storing the location information in the tracing target person traffic line information memory 20 when the control right of the controller 30 of the traffic line tracing apparatus (not illustrated) is transferred to the disease management authority terminal 55. Such moving and storing is preferably performed each time the communication connection verifier 90a determines that the tracing target person re-entered the residence.

In addition, the memory scheduler 19 drives the digital communication module 8 to generate wireless communication connection between the mobile phone 89 and the voice recognition terminal 17 (mobile phone-to-voice terminal communication mode) each time the mobile phone location information stored on the resident memory 89b is updated or at certain time intervals, and, at each time, reads the mobile phone location information stored on the resident memory 89b to move and store the read mobile phone location information in the storage space of the voice recognition terminal 17. Further, after storing and moving is completed, the traffic line tracing management application 89a preferably deletes the mobile phone location information stored in the resident memory 89b. In this way, by deleting the mobile phone location information stored in the resident memory 89b by the traffic line tracing management application 89a, the privacy of the tracing target person can be maximally protected.

In addition, the memory scheduler 19 is characterized by, when the control right of the traffic line tracing apparatus (not illustrated) is transferred to the disease management authority terminal 55, driving the digital communication module 8 to communicate with the remote server 200, reading traffic line history information of the tracing target person from the remote server 200 at predetermined time intervals (regularly) to move and store the traffic line history information in the tracing target person traffic line information memory 20, and deleting content of the remote server after completion of moving and storing.

When the memory scheduler 19 regularly deletes the traffic line history information of the tracing target person stored in the remote server 200, the privacy of the tracing target person can be protected.

Meanwhile, the memory scheduler 19 may regularly delete content stored in the tracing target person traffic line information memory which has passed an expiration date (for example, 4 weeks or more after initial storage). Therefore, in this case, when the memory scheduler 19 regularly deletes the traffic line history information of the tracing target person stored in the tracing target person traffic line information memory, the privacy of the tracing target person can be protected.

In addition, the memory scheduler 19 is characterized by, when the control right of the traffic line tracing apparatus transferred to the disease management authority is terminated (cancelled), automatically deleting all content stored in the remote server 200 and the tracing target person traffic line information memory 20.

Figure 3A:
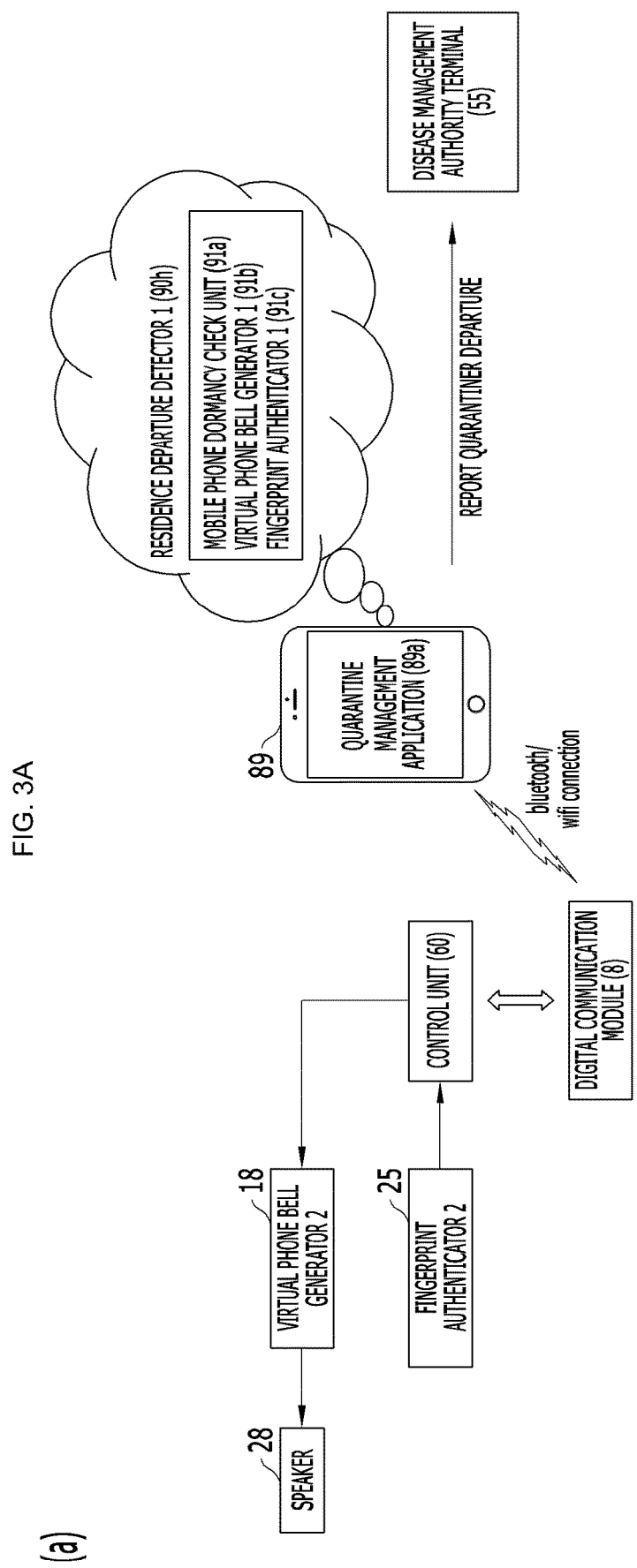
FIGS. 3A and 3B are diagrams schematically illustrating an example in which whether a quarantiner leaves a residence is verified using residence departure detectorapparatus of the distributed type traffic line tracing apparatus according to the embodiment of the present application, and when the quarantiner leaves the residence, a controller or a mobile phone reports departure of the quarantine.
Figure 3B:
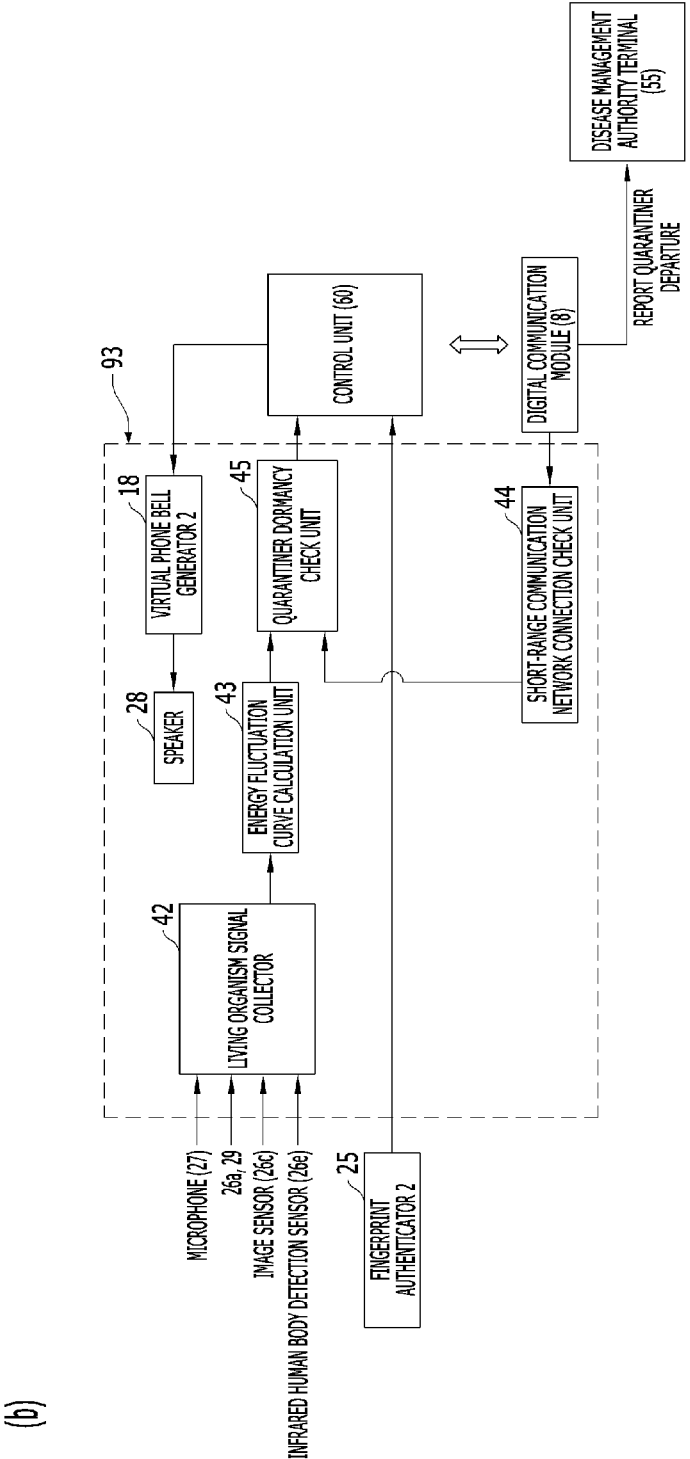

FIGS. 3A and 3B are diagrams schematically illustrating an example in which whether the quarantiner left the residence is verified using residence departure detector of the distributed type traffic line tracing apparatus according to the embodiment of the present application, and when the quarantiner left the residence, the controller or the mobile phone reports departure of the quarantiner.

Referring to FIG. 3A, the residence departure detector 1 (90h) may check the strength of a short-range wireless communication connection between the mobile phone 89 of the quarantiner and the digital communication module 8. In this instance, when the strength of a communication connection signal is greater than or equal to a reference value, it is possible to determine whether the quarantiner is actually in the residence even though the mobile phone 89 of the quarantiner is provided in the residence. When it is determined that the quarantiner left the residence, the residence departure detector 1 (90*h*) may report the departure of the quarantiner to the disease management authority terminal 55.

The residence departure detector 1 (90*h*) may include a mobile phone dormancy checker 91*a*, a virtual phone bell generator 1 (91*b*), and a virtual phone bell generator 2 (18).

The mobile phone dormancy checker 91*a* may check the frequency of shaking of the mobile phone according to walking movement of the quarantiner and the frequency of using touch of a mobile phone touch pad to check a dormant state of the mobile phone in which there is no movement of the quarantiner relative to the mobile phone 89.

In addition, when the mobile phone of the quarantiner is determined to be in the dormant state by the mobile phone dormancy checker 91*a*, the virtual phone bell generator 1 (91*b*) and the virtual phone bell generator 2 (18) can generate virtual phone bell sound in the mobile phone 89 of the quarantiner and the speaker 28.

When the quarantiner does not receive a call even though the virtual phone bell sound is repeatedly generated several times during the mobile phone dormant state, the residence departure detector 1 (90*h*) may determine that the quarantiner has left the residence without the mobile phone, and report the quarantiner departure to the disease management authority terminal 55.

Meanwhile, FIG. 3B is an example in which whether the quarantiner has left the residence is verified using the residence departure detector 2 (93), and a controller 60 reports the quarantiner departure when the quarantiner has left the residence.

FIG. 3B is an example in which when the mobile phone 89 of the quarantiner is operating abnormally (for example, when it is suspected that the quarantiner has left the residence, when a battery is discharged or the mobile phone is broken, or when the mobile phone power is turned OFF), whether the quarantiner is staying in the residence is verified by the residence departure detector 2 (93), and the controller 60 reports quarantiner departure when the quarantiner left the residence.

The residence departure detector 2 (93) may include living organism signal collector 42, an energy fluctuation curve calculator 43, a short-range communication network connection checker 44, a quarantiner dormancy checker 45, and a virtual phone bell generator 2 (18).

The living organism signal collector 42 may include at least one of a thermal imaging camera 26*a* for determining whether the quarantiner is present in a given space by observing an image change in a thermal image, an image sensor 26*c* for knowing the presence or absence of movement of the quarantiner by checking an image variation, an infrared human body detection sensor 26*e* that detects the presence or absence of movement of the quarantiner by checking a fluctuation of infrared rays emitted from the body of the quarantiner, and the microphone 27 for determining whether breathing sound or living sound of the quarantiner is present.

In addition, the energy fluctuation curve calculator 43 may calculate a time-dependent energy fluctuation from a signal obtained from the living organism signal collector 42.

In addition, the short-range communication network connection checker 44 may verify whether short-range wireless communication connection to the mobile device of the quarantiner is performed by the digital communication module 8.

In addition, when it is determined by the short-range communication network connection checker 44 that the mobile device of the quarantiner is not in the residence or the energy fluctuation continues at the reference value or less for a predetermined time period or more, the quarantiner dormancy checker 45 may determine that the quarantiner is in a quarantiner dormant state in which there is no movement of the quarantiner.

In addition, when the quarantiner dormancy checker 45 determines that the quarantiner is in the dormant state, the virtual phone bell generator 2 (18) may generate virtual phone bell sound in the speaker 28.

When the quarantiner does not receive a call even though the virtual phone bell is repeatedly generated several times while the quarantiner is in the dormant state, the residence departure detector 2 (93) may determine that the quarantiner has left the residence without the mobile phone, and report the quarantiner departure to the disease management authority terminal 55 through the digital communication module 8.

The infrared human body detection sensor 26*e* of the present disclosure may be replaced with the infrared temperature sensor 29.

As an example, the energy fluctuation curve calculator 43 may calculate time-dependent sound energy for the breathing sound or living sound of the quarantiner obtained from the microphone 27, or a time-dependent variable energy value on a thermal image according to a change in movement of the quarantiner obtained from the thermal imaging camera 26*a*.

In addition, the energy fluctuation curve calculator 43 may detect the quantity of infrared rays emitted from the infrared human body detection sensor 26*e* to the body of the quarantiner and calculate a time-dependent fluctuation energy value according to the change in movement of the quarantiner.

In addition, the energy fluctuation curve calculator 43 may calculate a time-dependent fluctuation energy value on an image according to a change in movement of the quarantiner obtained from the image sensor. The fluctuation energy can determine the degree of movement or bio-signals generated from the quarantiner, and thus it is possible to determine whether the quarantiner is present in the residence.

It is preferable that the residence departure detector 1 (90*h*) and the residence departure detector 2 (93) are activated between 8:00 am and 10:00 pm with bedtime being excluded.

Referring to FIGS. 3A and 3B, it is preferable that the phone is received by fingerprint authentication of the quarantiner using either a fingerprint authenticator 1 (91*c*) or a fingerprint authenticator 2 (25). For example, the phone bell sound may include a voice message (for example, "Please authenticate your fingerprint.") requesting fingerprint authentication from the quarantiner.

The fingerprint authenticator 2 (25) is authentication using a sensor that recognizes a fingerprint installed in the residence, and may be useful when the quarantiner does not remember a place where the mobile phone of the quarantiner is put.

According to the embodiment of the present application, referring to FIG. 6, the distributed type traffic line tracing apparatus (not illustrated) may be converted into an information collection adapter (reference symbol 33 of FIG. 6) modularized by being installed with the speaker 28, the microphone 27, the infrared human body detection sensor 26*e*, the thermal imaging camera 26*a*, the infrared temperature sensor 29, the image sensor 26*c*, and the fingerprint authenticator 2 (25) and installed in each of several individual spaces within the residence of the quarantiner, for example, in a living room, a master room, or other rooms. In this case, the information collection adapter (reference symbol 33 of FIG. 6) may be connected to the digital communication module 8 based on the Internet of Things to verify whether the quarantiner left the residence.

Therefore, the information collection adapter (reference symbol 33 of FIG. 6) is useful in the case of verifying whether the quarantiner left the residence when there are several individual spaces in the residence of the quarantiner.

FIG. 4A is a diagram schematically illustrating an example of the QR code register of the distributed type traffic line tracing apparatus according to the embodiment of the present application, in which a QR address is stored in the memory residing on the mobile phone by converting a QR code into a corresponding visited place address.

Referring to FIG. 4A, the QR code register 90*c* is characterized by determining whether or not an image captured by the camera of the mobile phone 89 is a QR code and requesting fingerprint authentication from the tracing target person in the case of an image of a QR code 70, so that in response to the tracing target person authenticating a fingerprint 88 on the mobile phone, a picture of the QR code 70 of the corresponding visited place (for example, Itaewon Club) is automatically captured and decoded, and visit time information along with information about the QR code is automatically stored in the memory 89*b* residing on the mobile phone.

In addition, another example of the QR code register 90*c* may determine whether the image captured by the mobile phone 89 is a QR code, and request fingerprint authentication from the tracing target person when the image is the QR code 70. In addition, the QR code register 90*c* may send the QR code 70 to a QR code-to-address conversion server 71 that converts the QR code 70 into an address in response to the tracing target person authenticating the fingerprint 88 on the mobile phone, receive a QR address decoded to an address in return, and automatically store the visit time information along with the QR address in the memory 89*b* residing on the mobile phone.

By allowing the picture of the QR code 70 to be automatically captured only by a procedure of authenticating the fingerprint 88 by the owner of the mobile phone, it is possible to solve a security problem caused by the abuse of the QR code.

Meanwhile, when the QR code or the QR address is successfully stored in the memory 89*b* residing on the mobile phone, the QR code register 90*c* may provide (display) a success message 87 indicating success in registration of a barcode or QR code allowing access to the visited place on the screen of the mobile phone 89.

In addition, the success message 87 may be a QR code indicating success of QR code registration or a QR code including address information of the visited place.

In addition, another aspect of the success message 87 may include a colored QR code, an entrance ticket (admission ticket), a QR code for an admission ticket, a discount coupon, or an advertisement text of a visited place.

For example, when the tracing target person turns ON the camera of the mobile phone and puts the mobile phone close to a QR code of the visited place (for example, Itaewon Club) on a wall sticker, the QR code register 90*c* requests mobile phone fingerprint authentication from the tracing target person. When fingerprint authentication is successful, a Web site corresponding to the QR code is directly connected, and a success message for access, such as a discount coupon, an advertisement for the visiting place, and an admission ticket, is received and displayed on a display window of the mobile phone.

In this case, a QR code inspector (for example, Itaewon Club manager) may visually check the success message (for example, admission ticket 87*a*) displayed on the display window on the mobile phone or scan a QR code 87*b* (for example, QR code for admission ticket) to recognize that the visitor has successfully completed (finished) registration of the QR code, and allow entrance of the visitor.

It is preferable to register the QR code both when entering and leaving the visited place. By checking in and out by registering the QR code before entering or leaving the visited place, it is possible to know a stay section (time section from entrance to exit) indicating a start time and an end time of stay of the tracing target person in the corresponding building.

In addition, in the QR code register 90*c*, it is preferable that when a new Bluetooth beacon signal is detected or a new Wi-Fi ID is detected by the communication connection verifier 90*a*, a pop-up window requesting permission to activate the mobile phone camera for capturing the picture of the QR code 70 from the tracing target person is automatically displayed on the display window of the mobile phone.

FIG. 4B is a diagram schematically illustrating an example in which key codes provided from mobile phones 100*b* of nearby contacts by Bluetooth beacons are stored in the resident memory 89*b* on the mobile phone 89 of the tracing target person, and the key codes stored in the resident memory 89*b* are moved and stored in the voice recognition terminal 17 through a wireless connection with the voice recognition terminal 17.

In the present embodiment, the traffic line tracing management application 89*a* installed on the mobile phone 89 of the tracing target person may include building stay section setter 90*k*. The building stay section setter 90*k* can calculate a stay section indicating a start time and an end time of stay of the mobile phone 89 of the tracing target person in the corresponding building by tracing and checking location information or location ID information provided from the location information provider 100.

For example, referring to FIG. 4B, the building stay section setter 90*k* can calculate the stay section indicating the start time and the end time of stay of the mobile phone 89 of the tracing target person in the corresponding building by tracing and checking information about the location ID (Bluetooth transmitter ID, Wi-Fi ID, or QR code) provided by the Bluetooth transmitter 100*f*, a QR code 100*a*, or Wi-Fi 100*c* installed in the building.

In addition, the building stay section setter 90*k* can know when the mobile phone 89 of the tracing target person entered and left the building by combining location ID information and GPS coordinates or location information of the base station. For example, it is particularly useful in the case where the QR code registration procedure is performed when entering and the QR code registration procedure is not performed when leaving (exiting). In this case, the building stay section setter 90*k* may store GPS coordinates at the time of entry according to the QR code registration procedure, and determine that exiting has occurred when current GPS coordinates deviate beyond a predetermined range from the GPS coordinates at the time of entry.

The mobile phone 89 of the tracing target person may read a plurality of key codes acquired from the mobile phones 100*b* of the nearby contacts stored on the resident memory 89*b* acquired during the building stay section through wireless communication connection with the voice recognition terminal 17 at the end of stay of the corresponding building calculated by the building stay section setter 90k, and move and store the plurality of key codes in the storage space (for example, traffic line information memory of the tracing target person) of the voice recognition terminal 17. In addition, building stay section information may be read together and stored in the storage space of the voice recognition terminal 17.

It is preferable that after moving and storing in the storage space of the voice recognition terminal 17, the traffic line tracing management application 89a deletes the key codes, location information, and location ID information stored on the resident memory 89b.

FIG. 5 is a diagram schematically illustrating the voice recognition terminal having a built-in Internet router of the distributed type traffic line tracing apparatus according to the embodiment of the present application.

(a) and (b) of FIG. 5 schematically illustrate an example in which the distributed type traffic line tracing apparatus is converted into the voice recognition terminal 17.

The voice recognition terminal 17 described below with reference to FIG. 5 preferably incorporates and integrates the digital communication module, the confirmed person traffic line information memory, the tracing target person traffic line information memory, the traffic line coincidence determiner, the memory scheduler, the control right transferer, and the controller inside the voice recognition terminal.

Referring to FIG. 5, the voice recognition terminal 17 may be installed in a region within the residence of the tracing target person. In addition, the voice recognition terminal 17 not only provides various contents to the digital TV 300 through a high-speed Internet connection, but also includes the voice recognizer 27a and the voice reproducer 28a to control the digital TV 300 by a voice command using the microphone 27 and provide a voice feedback service through the speaker 28. In addition, in order to trace the traffic line of the tracing target person, the voice recognition terminal 17 may include the digital communication module 8, the confirmed person traffic line information memory 21, the tracing target person traffic line information memory 20, the traffic line coincidence determiner 22, the memory scheduler 19, the control right transferer 32, the controller 30, and the body heat check diagnoser 26 on the inside.

In addition, reference symbol 25 denotes the fingerprint authenticator 2 (25) that performs identity authentication by verifying whether a fingerprint input from the fingerprint sensor matches a fingerprint of the tracing target person (or quarantiner) registered in advance.

According to the embodiment of the present application, the control right transferer 32 is characterized in that in case of national emergency, especially in an emergency situation such as infectious disease pandemic, in response to a request from the disease management authority terminal, the tracing target person performs an approval process for transferring the control right of the controller 30 of the traffic line tracing apparatus to the disease management authority terminal.

In addition, the control right transferer 32 is characterized by, in the case where the control right of the traffic line tracing apparatus is transferred to the disease management authority terminal 55, when the traffic line of the confirmed person coincides with the traffic line of the tracing target person, allowing the controller 30 to automatically declare and report the fact that the tracing target person is the quarantining target person to the disease management authority using the digital communication module.

In addition, the control right transferer 32 is characterized by, in the case where the control right of the traffic line tracing apparatus is transferred to the disease management authority terminal, when the tracing target person is determined to be the quarantiner, allowing the disease management authority terminal 55 to read latest traffic line history information of the tracing target person stored in the tracing target person traffic line information memory 20.

In addition, the control right transferer 32 is characterized by, in the case where the control right of the traffic line tracing apparatus is transferred to the disease management authority, when the tracing target person is determined to be the quarantining target person, allowing the controller 30 to drive the digital communication module 8 to transmit latest traffic line history information of the tracing target person stored in the tracing target person traffic line information memory 20 to the disease management authority terminal.

When the tracing target person is determined to be the quarantining target person, content transmitted to the disease management authority terminal is a digitized message signal and may include information (for example, traffic line history information, residence address, name, age, gender, mobile phone number, e-mail address, resident registration number, etc. stored in the tracing target person traffic line information memory) of the tracing target person determined to be the quarantining target person. Meanwhile, a control right transfer approval process is preferably performed through the traffic line tracing management application 89a on the mobile phone 89 of the tracing target person, and it is preferable that the disease management authority terminal 55 requests the transfer of the control right, the tracing target person accepts this request on the traffic line tracing management application by fingerprint authentication, and then the traffic line tracing management application notifies the controller 30 that the control right is transferred through wireless communication with the digital communication module 8 and activates the memory scheduler 19, thereby completing the control right transfer approval procedure.

(a) of FIG. 5 is an example in which the thermal imaging camera 26a is applied to the voice recognition terminal 17 to measure the body heat of the tracing target person.

Referring to (a) of FIG. 5, it is preferable that the thermal imaging camera 26a obtains an image of the image sensor 26c by overlaying the image on a thermal image. In this case, a clear image having better expressed outline boundary and details is obtained, which is advantageous for face recognition. Besides, when the body heat is measured, it is possible to more precisely perform thermal imaging camera image pixel selection corresponding to the forehead from the face image.

In addition, the thermal imaging camera image pixel selection corresponding to the forehead from the face image can be performed in consideration of a normal arrangement correlation between eyes, a nose, a mouth and a forehead in the face image.

(b) of FIG. 5 is an example in which the infrared temperature sensor 29 is applied to the voice recognition terminal 17 to measure the body heat from the forehead of the tracing target person. A cylindrical display device 23 may visually display virtual eyes 24a and 24b and mouth 24c in order to induce correct alignment between the forehead of the tracing target person and the infrared temperature sensor 29.

Meanwhile, the image sensor 26c is installed inside the cylindrical display device 23, and can capture an image of the virtual eyes 24a and 24b and mouth 24c displayed on the cylindrical display device 23 and an image of the eyes and mouth of the tracing target person overlaying each other.

In addition, alignment information provider 39 may determine how well image alignment is performed between the two overlaid images from the overlaid images, and provide feedback information to the tracing target person.

When an overlaid image generated based on the image of the virtual eyes and mouth and the image of the eyes and mouth of the tracing target person is well aligned within a predetermined range, the infrared temperature sensor 29 may measure the body heat by measuring infrared rays emitted from the forehead of the tracing target person. When the image is well aligned, the infrared temperature sensor 29 automatically achieves correct measurement alignment with the forehead of the tracing target person.

As the cylindrical display device 23, it is possible to use a cylindrical magic mirror or a transparent organic light emitting diodes (OLED) display panel.

For example, the magic mirror is a plate glass made of a semi-permeable film by plating silver or tin on one side of the plate glass. Further, the magic mirror looks like a mirror on a bright side, and the opposite side of the magic mirror can be seen through from a dark side. The image sensor 26c can well observe the face of the tracing target person and the virtual eyes 24a and 24b and mouth 24c present on the outside at the same time through the magic mirror from the inside of the cylindrical display device 23.

In addition, positions of the virtual eyes 24a and 24b and mouth 24c visually displayed on the transparent OLED display panel can be selected so that the positions are close to actual positions of the eyes and mouth of the tracing target person identified by the fingerprint authenticator 2 (25).

The image sensor 26c can simultaneously observe the face of the tracing target person and the virtual eyes 24a and 24b and mouth 24c present on the outside from the inside of the transparent OLED display panel.

FIG. 6 is an example schematically illustrating an information collection adapter of the distributed type traffic line tracing apparatus according to the embodiment of the present application provided with connection to the digital communication module through Bluetooth, Wi-Fi or Internet of Things connection for each individual living space in the residence. In other words, FIG. 6 is an example of the information collection adapter 33 modularized by being installed with the microphone 27, the infrared human body detection sensor 26e, the fingerprint authenticator 2 (25), and the speaker 28 provided with connection to the digital communication module 8 through Bluetooth, Wi-Fi or Internet of Things connection for each individual living space in the residence.

According to the embodiment of the present application, the information collection adapter 33 may include a power outlet connection terminal 37c providing electrical connection with a power outlet 37d to supply power to the information collection adapter 33, and a circuit (not illustrated) for connection with the digital communication module 8 by Bluetooth, Wi-Fi, or Internet of Things.

FIG. 6A illustrates a front view and a side view of the information collection adapter 33, and FIG. 6B illustrates an example in which the information collection adapter 33 is activated by electrical connection between the power outlet 37d and the power connection terminal 37c of the information collection adapter 33 so that the information collection adapter 33 is connected to the digital communication module 8 by Bluetooth/Wi-Fi/Internet of Things.

Reference symbol 28 illustrated in FIG. 6 is a speaker installed for each individual space in the residence of the quarantiner, which is connected to the digital communication module 8 by communication connection and can deliver a voice message requesting fingerprint authentication to the individual space. The quarantiner can notify the controller 60 that the quarantiner is present in the residence by listening to the voice message and responding through the fingerprint authenticator 2 (25).

Figure 7:
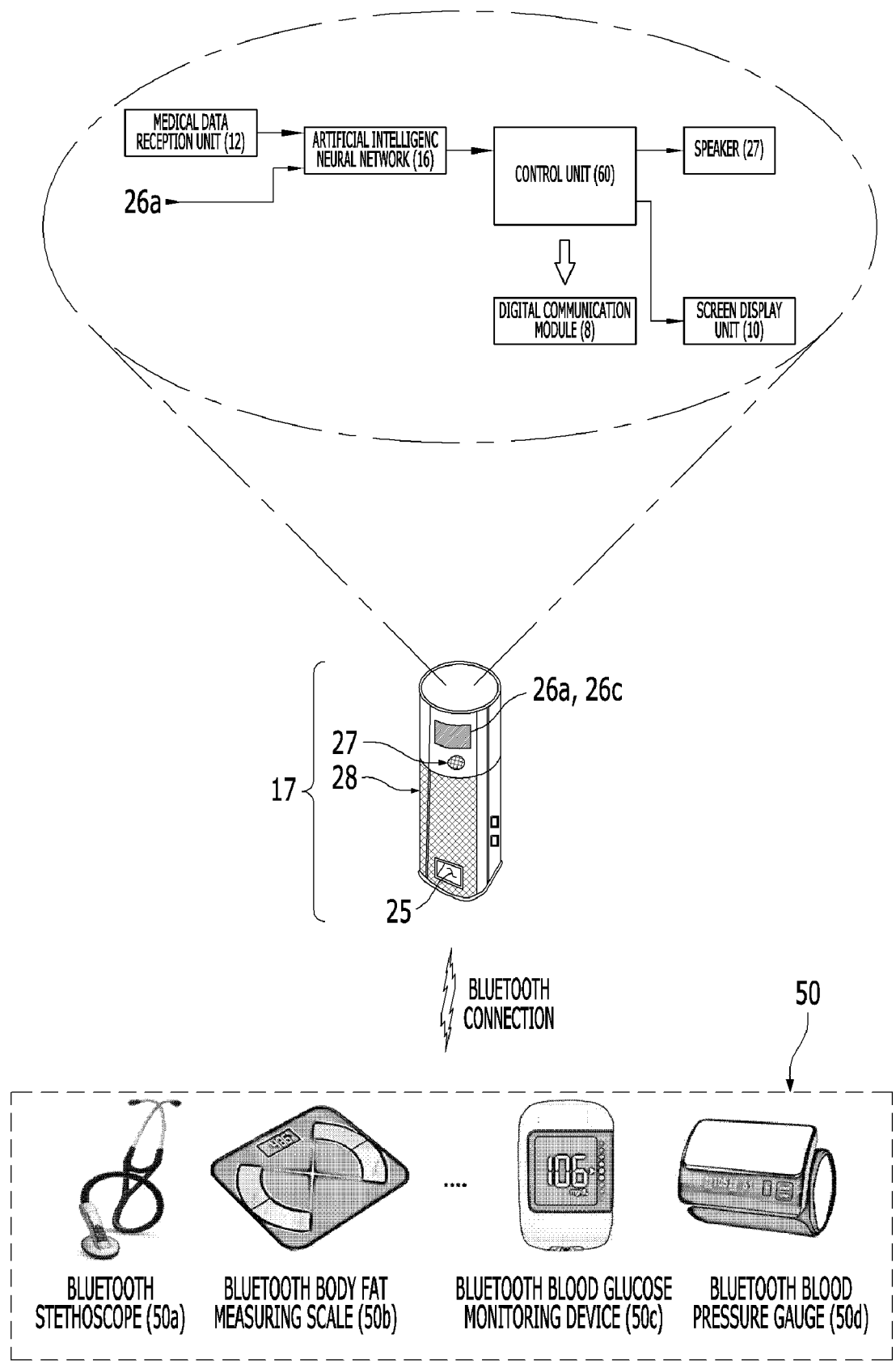
FIG. 7 is a diagram schematically illustrating an example of performing a telemedicine diagnosis based on a plurality of medical devices using the distributed type traffic line tracing apparatus according to the embodiment of the present application.

FIG. 7 is a diagram schematically illustrating an example of performing a telemedicine diagnosis based on a plurality of medical devices using the distributed type traffic line tracing apparatus according to the embodiment of the present application. In other words, FIG. 7 illustrates an example in which various medical devices 50 are connected to the voice recognition terminal 17 by Bluetooth, and the voice recognition terminal 17 includes an artificial intelligence neural network 16 to diagnose a patient.

According to the embodiment of the present application, the voice recognition terminal 17 may include the digital communication module 8 providing a short-range communication connection (Bluetooth connection) with the medical devices 50, a medical data receptor 12 that receives medical data measured from a patient by the medical devices 50 through the digital communication module 8, and the artificial intelligence neural network 16 subjected to deep learning in advance by medical data for training.

The embodiment of the present application is characterized in that various contents are provided to the digital TV 300 through a high-speed Internet connection and the voice recognition terminal 17 that controls the digital TV 300 by a voice command performs remote diagnosis.

The voice recognition terminal 17 may include the digital communication module 8 that provides an Internet and Wi-Fi communication connection that allows telemedicine diagnosis with a medical professional or provides a short-range communication connection (Bluetooth connection) with a medical device.

In addition, the voice recognition terminal 17 may include a screen displayer 10 for sharing a screen between a patient and a medical professional during a telemedicine diagnosis.

In addition, the voice recognition terminal 17 may include the medical data receptor 12 that receives medical data information measured from the patient by the medical device.

In addition, the voice recognition terminal 17 may include the artificial intelligence neural network 16 subjected to deep learning in advance using medical data for training.

In addition, the voice recognition terminal 17 may include the speaker 28 for providing a guideline on health management, a telemedicine diagnosis method, and a guideline on a method of using a medical device to the patient.

Meanwhile, the voice recognition terminal 17 may automatically determine the presence or absence of a disease of the patient and the risk of the disease by applying health medical data of the patient collected from the plurality of medical devices 50 to the artificial neural network subjected to deep learning.

In addition, the artificial intelligence neural network 16 subjected to deep learning may analyze medical data received by the medical data receptor 12 to automatically determine the presence or absence of a disease of the patient and the risk of the disease.

In addition, the controller 60 is characterized by controlling the digital communication module 8, the speaker 28, and the screen displayer 10 to provide a guideline for health management and a guideline for a method of using the medical device to the patient according to a health condition of the patient based on a medical data analysis result from the artificial intelligence neural network 16.

In addition, the controller 60 determines the necessity of telemedicine diagnosis according to the health condition of the patient based on the medical data analysis result from the artificial intelligence neural network 16, and controls the digital communication module 8, the speaker 28, and the screen displayer 10 to perform telemedicine diagnosis between the doctor and the patient if necessary.

Reference symbol 50a denotes a stethoscope, reference symbol 50b denotes a body fat measuring scale, reference symbol 50c denotes a blood glucose monitoring device, and reference symbol 50d denotes a blood pressure gauge.

According to the embodiment of the present application, each of the plurality of medical devices 50 is a device having a wireless transmitter (for example, Bluetooth) that transmits medical data measured from a specimen or an affected area of the patient to the medical data receptor, and may include at least one of medical devices selected from an ultrasound scanner, a heart pulse sensor, a stethoscope, a thermal imaging camera, a thermometer, a urine tester, a stool tester installed in a toilet, a breast cancer diagnosis device, a blood pressure gauge, a diabetograph, a weight scale, a body fat analyzer, a mobile phone camera for taking pictures around a tonsils and uvula in an oral cavity to check for sore throat, a mobile phone camera for taking pictures of teeth in a mouth for dental examination, a handheld device for filling out questionnaires asking for a health condition, an eye test measurement device, an automated blood analyzer, a DNA amplification test device, a virus diagnostic kit device that diagnoses using specific antigens of virus, a rapid test device, a wearable device, and a cancer diagnostic device.

Meanwhile, the voice recognition terminal 17 may use a thermal image of a breast area obtained by the thermal imaging camera 26a to determine a risk of breast cancer of a patient using the artificial intelligence neural network 16 subjected to learning in advance by pattern images of the thermal image coming from a tumor in the breast area.

For example, the patient may take an orally administered imaging agent containing a contrast material that only adheres to breast cancer cells, and then heat from the breast area of the patient obtained from the thermal imaging camera 26a may be detected to calculate a risk of breast cancer of the patient using the artificial intelligence neural network 16 subjected to deep learning for diagnosing the breast cancer.

FIG. 8 is a diagram schematically illustrating an example of a telemedicine diagnosis in which a doctor remotely checks a health condition of a fetus using the distributed type traffic line tracing apparatus according to the embodiment of the present application and the stethoscope among the plurality of medical devices. In other words, FIG. 8 is an example of telemedicine diagnosis in which a doctor 201 remotely checks a health condition of a fetus of a mother 86 using the voice recognition terminal 17 connected to the stethoscope 61 via Bluetooth.

According to the embodiment of the present application, the voice recognition terminal 17 may include the digital communication module 8 that provides an Internet and Wi-Fi communication connection that allows telemedicine diagnosis with a medical professional, that is, the doctor 201, or provides a short-range communication connection (Bluetooth connection) with the stethoscope 61, the fingerprint authenticator 2 (25) for authenticating the identity of the mother 86, the medical data receptor 12 that receives medical data measured from the mother by the stethoscope 61, the artificial intelligence neural network 16 subjected to deep learning in advance by medical data for training, the digital communication module 8 for performing telemedicine diagnosis between the doctor 201 and the mother 86, and the controller 60 that controls the speaker 28 and the screen displayer 10.

The voice recognition terminal 17 provides visual information useful for telemedicine diagnosis during the telemedicine diagnosis to the screen displayer 10 to share a screen between the mother 86 and the medical professional, that is, the doctor 201. In addition, the voice recognition terminal 17 may provide a guideline for health management, a telemedicine diagnosis method, and a stethoscope usage to the mother through the speaker 28. In addition, the artificial intelligence neural network 16 subjected to deep learning may analyze medical data from the stethoscope 61 received by the medical data receptor 12 to automatically determine the presence or absence of a disease in the mother and fetus and the risk of the disease.

Further, the controller 60 may drive the digital communication module 8 so that information displayed on the screen displayer 10 and information the doctor sees on the monitor 206 are the same.

In this case, the doctor shares real-time information with the mother 86 through the monitor 206 so that the doctor can directly instruct the mother 86 about a method of using the stethoscope 61 through the communication network 202, thereby helping the mother diagnose the fetal health as if the doctor 201 is next to the mother 86.

Reference symbol 60 denotes a headphone, which allows the doctor to remotely listen to the heart pulse of the fetus from the stethoscope 61.

Hereinafter, based on the details described above, an operation flow of the present application will be briefly described.

Although not illustrated in the drawings, a distributed type traffic line tracing method may be performed by the distributed type traffic line tracing apparatus and the voice recognition terminal 17 described above. Therefore, even when omitted below, the description of the distributed type traffic line tracing apparatus and the voice recognition terminal 17 may be equally applied to the description of the distributed type traffic line tracing method. Hereinafter, for convenience of description, the method will be described as being performed by the distributed type traffic line tracing apparatus (not illustrated).

In operation S101, the distributed type traffic line tracing apparatus (not illustrated) may register a Bluetooth or Wi-Fi connection between the mobile phone of the tracing target person and the digital communication module.

In operation S102, the terminal of the disease management authority may request the tracing target person for the control right of the traffic line tracing apparatus.

In operation S103, the tracing target person may transfer the control right of the distributed traffic line tracing apparatus or the traffic line tracing management application to the disease management authority based on transfer information generated through a predetermined authentication procedure through a computer application or a mobile application of the tracing target person.

In operation S104, when it is determined by the communication connection verifier that the tracing target person has left the residence and then re-entered, the distributed type traffic line tracing apparatus (not illustrated) may transmit the traffic line (location history information of the mobile phone) of the tracing target person stored in the resident memory on the mobile phone of the tracing target person to the digital communication module.

In operation S105, when a confirmed person occurs, the disease management authority terminal may transmit traffic line information of the confirmed person to the digital communication module.

In operation S106, when the traffic line of the tracing target person overlaps the traffic line of the confirmed person, the distributed type traffic line tracing apparatus (not illustrated) may report (provide) that the tracing target person is a quarantining target person to the disease management authority terminal.

In operation S107, the distributed type traffic line tracing apparatus (not illustrated) may send a notice reporting that the tracing target person has been confirmed as a quarantining target person to the mobile phone of the quarantining target person, and the quarantining target person may be confirmed by the quarantining target person browsing the notice by a fingerprint authentication procedure on the mobile phone.

In operation S108, when it is determined by the residence departure detector that the quarantiner has left the residence, the distributed type traffic line tracing apparatus (not illustrated) may provide a report on departure of the quarantiner to the disease management authority terminal.

In the above description, operations S101 to S108 may be further divided into additional operations or may be combined into fewer operations, depending on the embodiment of the present application. In addition, some operations may be omitted as necessary, and the order between operations may be changed.

The distributed type traffic line tracing method according to the embodiment of the present application may be implemented in the form of program instructions that can be executed through various computer means and recorded in a computer-readable medium. The computer-readable medium may include program instructions, data files, data structures, etc. alone or in combination. The program instructions recorded on the medium may be specially designed and configured for the present disclosure, or may be known and usable to those skilled in computer software. Examples of the computer-readable recording medium include hardware devices specially configured to store and execute program instructions such as magnetic media such as a hard disk, a floppy disk, and a magnetic tape, optical media such as a CD-ROM and a DVD, magnetic-optical media such as a floptical disk, a ROM, a RAM, and a flash memory, etc. Examples of program instructions include not only machine language codes such as those produced by a compiler, but also high-level language codes that can be executed by a computer using an interpreter, etc. The hardware devices described above may be configured to operate as one or more software modules to perform the operation of the present disclosure, and vice versa.

In addition, the above-described distributed type traffic line tracing method may be implemented in the form of a computer program or application executed by a computer stored in a recording medium.

According to the disclosure above for solving problems of the present application, by allowing a privately owned distributed type traffic line tracing apparatus to automatically report to a disease management authority only when a traffic line overlaps a traffic line of a confirmed person, a quarantining target person can be discovered and found early while protecting a privacy of an individual much more when compared to a centralized type, thereby rapidly establishing an infectious disease management system for patients with suspected diseases and efficiently managing the patients from the spread of infectious diseases.

However, the effect obtainable in the present application is not limited to the above-described effects, and other effects may exist.

The activity range checker, AP, artificial intelligence neural network, authenticator, base station, Bluetooth switcher, Bluetooth transmitter, body heat check diagnoser, body heat determinator, building stay section setter, checker, collector, communication connection verifier, confirmed person traffic line information memory, confirmer, connector, control right transferer, controller, detector, digital communication module, energy fluctuation curve calculator, face recognizer, fingerprint authenticator, generator, GPS, image sensor, infrared temperature sensor, living organism signal collector, medical data receptor, medical devices, memory, memory scheduler, mobile data connector, mobile phone, mobile phone dormancy checker, peripheral mobile phones, power outlet connection terminal, provider, QR code register, quarantiner confirmer, quarantiner dormancy checker, register, residence departure detector, setter, short-range communication network connection checker, stay validity filter, suspender, switcher, the digital communication module, the information collection adapter, thermal imaging camera, tracing target person traffic line information memory, traffic line coincidence determiner, traffic line tracing management application, verifier, virtual phone bell generator, voice recognition terminal, voice reproducer, voice terminal, Wi-Fi switcher in FIGS. 1-8 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-8 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A distributed type traffic line tracing system comprising:
    a traffic line tracing apparatus;
    a traffic line tracing management application installed in a mobile phone of a tracing target person, configured to control the mobile phone to:
        store a mobile phone location information of the tracing target person provided from a plurality of location information providers in a resident memory of the mobile phone; and
        wirelessly transmit the mobile phone location information to the traffic line tracing apparatus;
    wherein the traffic line tracing apparatus comprises:
    a digital communication module installed in a residence of the tracing target person;
    a communication connection verifier, configured to verify whether the digital communication module and the mobile phone are connected through short-range communication;
    a tracing target person traffic line information memory configured to store traffic line history information of the mobile phone;
    a memory scheduler configured to transfer the mobile phone location information stored in the resident memory to the tracing target person traffic line information memory through wireless connection between the digital communication module and the mobile phone;
    a confirmed person traffic line information memory configured to store traffic line information of infected persons provided from the disease management authority terminal through the digital communication module;

a traffic line coincidence determiner configured to determine whether there is an overlapping path between the tracing target person and the infected persons;
a processor configured to:
select the tracing target person as a self-quarantining target person when there is an overlapping path between the tracing target person and the infected persons; and
drive the digital communication module to transmit information related to the selected self-quarantining target person to a disease management authority terminal;
a control right transferer configured to transfer a control right of the processor to the disease management authority terminal; and
a residence departure detector configured to report suspected residence departure to the disease management authority terminal when the self-quarantining target person left the residence for a predetermined time or more,
wherein the residence departure detector includes
a virtual phone bell generator configured to generate a virtual phone bell sound when it is suspected that the self-quarantining target person left the residence, and
wherein, when the self-quarantining target person does not answer the virtual phone bell sound even though the virtual phone bell sound is output a predetermined number of times or more, the residence departure detector is further configured to determine that the self-quarantining target person has left the residence, and report self-quarantining target person departure to the disease management authority terminal.

2. The system according to claim 1, wherein the traffic line information of the infected persons includes any one or any combination of any two or more of pieces of location information selected from GPS coordinates on the traffic line of hand phones of the infected persons, a base station information accessed by the hand phones of the infected persons, QR codes of a visited place of the infected persons, key codes collected by the hand phone of the infected persons, Bluetooth transmitter IDs collected by the hand phone of the infected persons, Wi-Fi IDs accessed by the hand phone of the infected persons, and a stay duration information corresponding to the location information.

3. The system according to claim 1, wherein the traffic line history information of the mobile phone includes any one or any combination of any two or more pieces of location information selected from GPS coordinates on the traffic line of the mobile phone, a base station information accessed by the mobile phone, QR codes of a visited place of the tracing target person, key codes collected by the mobile phone, a Bluetooth transmitter IDs collected by the mobile phone, Wi-Fi IDs accessed by the mobile phone, and a stay duration information corresponding to the location information.

4. The system according to claim 3, wherein the traffic line tracing management application includes a stay validity filter configured to extract a valid location information among location information of the mobile phone provided from the plurality of location information provider, and store the valid location information in the resident memory on the mobile phone.

5. The system according to claim 4, wherein the stay validity filter is further configured to select the key codes generated the predetermined number of times or more per hour as a valid key code information.

6. The system according to claim 1, wherein the traffic line tracing management application includes a Wi-Fi switcher configured to force the mobile phone to temporarily switch to a Wi-Fi mode, search for Wi-Fi ID allowed to communicate with the mobile phone, and store the Wi-Fi ID in the resident memory on the mobile phone.

7. The system according to claim 1, wherein the traffic line tracing management application includes a Bluetooth switcher configured to force the mobile phone to temporarily switch to a Bluetooth scan mode, search for a Bluetooth transmitter ID allowed to communicate with the mobile phone, and store the Bluetooth transmitter ID in the resident memory on the mobile phone.

8. The system according to claim 1,
wherein the traffic line tracing management application includes a QR code register, and
wherein the QR code register is configured to capture a QR code information and automatically store the QR code in the resident memory on the mobile phone.

9. The system according to claim 1,
wherein the traffic line tracing management application includes a quarantiner confirmer configured to perform a fingerprint authentication procedure on the mobile phone, and
wherein the processor or the disease management authority terminal provides notification information of being selected as a quarantiner to the self-quarantining target person.

10. The system according to claim 1, wherein the plurality of location information providers includes a building address provided by geographic information system (GIS).

11. A traffic line tracing apparatus having a voice recognition terminal installed in a residence of a tracing target person, the voice recognition terminal comprising:
a speaker configured to provide voice feedback service;
a digital communication module configured to provide a communication connection between a disease management authority terminal and a mobile phone of the tracing target person;
a communication connection verifier configured to verify whether the digital communication module and the mobile phone are connected through short-range communication;
a tracing target person traffic line information memory configured to store traffic line history information of the mobile phone;
a memory scheduler configured to transfer a mobile phone location information stored in the mobile phone to the tracing target person traffic line information memory through wireless connection between the digital communication module and the mobile phone;
a confirmed person traffic line information memory configured to store traffic line information of infected persons provided from the disease management authority terminal through the digital communication module;
a traffic line coincidence determiner configured to determine whether there is an overlapping path between the tracing target person and the infected persons;
a processor configured to:
select the tracing target person as a self-quarantining target person when there is an overlapping path between the tracing target person and the infected persons, and
drive the digital communication module to transmit information related to the self-quarantining target person to the disease management authority terminal;

a control right transferer configured to transfer a control right of the processor to the disease management authority terminal; and a residence departure detector configured to report suspected residence departure to the disease management authority terminal when the self-quarantining target person left the residence for a predetermined time or more, wherein the residence departure detector includes a virtual phone bell generator configured to generate a virtual phone bell sound when it is suspected that the self-quarantining target person left the residence, and wherein, when the self-quarantining target person does not answer the virtual phone bell sound even though the virtual phone bell sound is output a predetermined number of times or more, the residence departure detector is further configured to determine that the self-quarantining target person has left the residence, and report self-quarantining target person departure to the disease management authority terminal.

12. The apparatus according to claim 11, wherein the voice recognition terminal further includes a body heat checking unit that includes:

a thermal imaging camera or an infrared temperature sensor configured to measure body heat by detecting heat radiation emitted from a body of the tracing target person.

13. The apparatus according to claim 11, wherein the voice recognition terminal further includes:

an infrared temperature sensor configured to measure body heat of the tracing target person; and a display device configured to visually display virtual eyes and mouth to guide correct alignment between a forehead of the tracing target person and the infrared temperature sensor.

14. The traffic line tracing apparatus according to claim 11 further includes:

living organism signal collector including at least one of a thermal imaging camera configured to determine whether the self-quarantining target person is present in a given space by observing an image change in a thermal image, an image sensor for knowing presence or absence of movement of the self-quarantining target person by checking an image variation, an infrared human body detection sensor that detects presence or absence of the self-quarantining target person and a microphone configured to detect breathing sound or living sound of the self-quarantining target person;

an energy fluctuation curve calculator configured to calculate a time-dependent energy fluctuation from a signal obtained from the living organism signal collector; and a self-quarantining target person dormancy checker configured to determine that the self-quarantining target person is in a dormant state either when it is determined by the communication connection verifier that the mobile device of the self-quarantining target person is not in the residence or when the energy fluctuation continues at a reference value or less for a predetermined time period or more.

15. The traffic line tracing apparatus according to claim 11, wherein the residence departure detector further includes a fingerprint authenticator, and wherein the fingerprint authenticator performs identification of the self-quarantining person through the fingerprint authentication procedure when the self-quarantining person answers the virtual phone bell sound.

16. A distributed type traffic line tracing method performed by the distributed type traffic line tracing apparatus of claim 1, the method comprising:

registering Bluetooth or Wi-Fi connection between a mobile phone of a tracing target person and a digital communication module in a residence;

transferring a control right of the distributed type traffic line tracing system to a disease management authority;

receiving traffic line information of infected persons from the disease management authority terminal through the digital communication module;

reporting the tracing target person as a self-quarantining target person to the disease management authority terminal when there is an overlapping path between the tracing target person and the infected persons; and reporting self-quarantining target person departure to the disease management authority terminal when it is determined by residence departure detector that the self-quarantining target person has left the residence, wherein the reporting self-quarantining target person departure includes:

generating a virtual phone bell sound when it is suspected that the self-quarantining target person left the residence, and determining that the self-quarantining target person has left the residence when the self-quarantining target person does not answer the virtual phone bell sound even though the virtual phone bell sound is output a predetermined number of times or more.

* * * * *